(12) United States Patent
Mullin et al.

(10) Patent No.: US 9,474,450 B2
(45) Date of Patent: Oct. 25, 2016

(54) TEMPERATURE MEASUREMENT SYSTEM

(71) Applicant: Welch Allyn, Inc., Skaneateles Falls, NY (US)

(72) Inventors: Matthew D. Mullin, Memphis, NY (US); John A. Lane, Weedsport, NY (US); David E. Quinn, Auburn, NY (US); Michael J. Anson, Syracuse, NY (US)

(73) Assignee: WELCH ALLYN, INC., Skaneateles Falls, NY (US)

( * ) Notice: Subject to any disclaimer, the term of this patent is extended or adjusted under 35 U.S.C. 154(b) by 0 days.

(21) Appl. No.: 14/186,797

(22) Filed: Feb. 21, 2014

(65) Prior Publication Data

US 2014/0171805 A1   Jun. 19, 2014

Related U.S. Application Data

(63) Continuation of application No. 13/569,867, filed on Aug. 8, 2012.

(51) Int. Cl.
| | | |
|---|---|---|
| *A61B 5/01* | (2006.01) | |
| *H05K 13/00* | (2006.01) | |
| *A61B 5/06* | (2006.01) | |
| *G01K 13/00* | (2006.01) | |

(52) U.S. Cl.
CPC ............. *A61B 5/01* (2013.01); *A61B 5/015* (2013.01); *A61B 5/067* (2013.01); *G01K 13/002* (2013.01); *H05K 13/00* (2013.01); *Y10T 29/49002* (2015.01)

(58) Field of Classification Search
CPC ........ A61B 5/01; A61B 5/015; A61B 5/067; Y10T 29/49002; G01K 13/002; H05K 13/00
See application file for complete search history.

(56) References Cited

U.S. PATENT DOCUMENTS

| | | | |
|---|---|---|---|
| 4,009,707 | A | 3/1977 | Ward |
| 4,036,211 | A | 7/1977 | Veth et al. |
| 4,054,057 | A | 10/1977 | Kluge |
| 4,365,307 | A | 12/1982 | Tatsuwaki et al. |
| 4,383,271 | A | 5/1983 | Berry et al. |
| 4,413,324 | A | 11/1983 | Tatsuwaki et al. |
| 4,450,479 | A | 5/1984 | Horne |

(Continued)

FOREIGN PATENT DOCUMENTS

| | | |
|---|---|---|
| DE | 19842403 | 3/2000 |
| DE | 19857145 A1 | 3/2000 |

(Continued)

OTHER PUBLICATIONS

Medioni et al., "Non-Cooperative Persons identification at a Distance with 3D Face Modeling" Biometrics: Theory, Applications, and Systems, 2007. BTAS 2007.*

(Continued)

*Primary Examiner* — Long V Le
*Assistant Examiner* — Colin T Sakamoto

(57) ABSTRACT

A method of determining a temperature of a patient includes measuring a first temperature of the patient with a temperature device, and measuring a second temperature of the patient. The method also includes determining a temperature value indicative of a core temperature of the patient based on at least one of the first and second temperatures.

21 Claims, 8 Drawing Sheets

(56) References Cited

U.S. PATENT DOCUMENTS

| | | |
|---|---|---|
| 4,494,550 A | 1/1985 | Blazek et al. |
| 4,594,507 A | 6/1986 | Elliott et al. |
| 4,700,708 A | 10/1987 | New, Jr. et al. |
| 4,737,917 A | 4/1988 | Perron |
| 4,754,139 A | 6/1988 | Ennulat et al. |
| 4,784,149 A | 11/1988 | Berman et al. |
| 4,806,761 A | 2/1989 | Carson et al. |
| 4,895,164 A | 1/1990 | Wood |
| 4,993,424 A | 2/1991 | Suszynski et al. |
| 5,018,872 A | 5/1991 | Suszynski et al. |
| 5,086,220 A | 2/1992 | Berthold et al. |
| 5,091,646 A | 2/1992 | Taylor |
| 5,127,742 A | 7/1992 | Fraden |
| 5,214,489 A | 5/1993 | Mizutani et al. |
| 5,272,340 A | 12/1993 | Anbar |
| 5,274,235 A | 12/1993 | Taylor |
| 5,274,489 A | 12/1993 | Smith et al. |
| RE34,507 E | 1/1994 | Egawa et al. |
| 5,289,006 A | 2/1994 | Gal |
| 5,293,877 A | 3/1994 | O'Hara et al. |
| 5,368,392 A | 11/1994 | Hollander et al. |
| 5,420,428 A | 5/1995 | Bullington et al. |
| 5,438,199 A | 8/1995 | Agam et al. |
| 5,469,855 A | 11/1995 | Pompei et al. |
| 5,524,984 A | 6/1996 | Hollander et al. |
| 5,530,246 A | 6/1996 | Hawkins |
| 5,532,555 A | 7/1996 | Yamada |
| 5,561,295 A | 10/1996 | Jacksen et al. |
| 5,626,147 A | 5/1997 | Lackey |
| 5,632,555 A | 5/1997 | Gregory et al. |
| 5,645,349 A | 7/1997 | Fraden |
| 5,653,537 A | 8/1997 | Ignatowicz et al. |
| 5,686,779 A | 11/1997 | Vig |
| 5,727,880 A | 3/1998 | Hollander et al. |
| 5,729,019 A | 3/1998 | Krafthefer et al. |
| 5,743,644 A | 4/1998 | Kobayashi et al. |
| 5,747,863 A | 5/1998 | Shoda |
| 5,790,586 A | 8/1998 | Hilton, Jr. et al. |
| 5,820,264 A | 10/1998 | Tsao et al. |
| 5,823,678 A | 10/1998 | Hollander et al. |
| 5,847,832 A | 12/1998 | Liskow et al. |
| 5,902,044 A | 5/1999 | Pricer et al. |
| 6,011,891 A | 1/2000 | Katzir et al. |
| 6,022,140 A | 2/2000 | Fraden et al. |
| 6,272,375 B1 | 8/2001 | Katzir et al. |
| 6,631,287 B2 | 10/2003 | Newman et al. |
| 6,789,936 B1 | 9/2004 | Kraus et al. |
| 6,898,457 B1 | 5/2005 | Kraus et al. |
| 6,991,368 B2 | 1/2006 | Gerlitz |
| 7,354,399 B2 | 4/2008 | Strom et al. |
| 7,597,668 B2 | 10/2009 | Yarden |
| 7,651,266 B2 | 1/2010 | Bellifemine |
| 7,813,889 B2 | 10/2010 | Quinn et al. |
| 2002/0143251 A1 | 10/2002 | Richardson et al. |
| 2002/0143257 A1 | 10/2002 | Newman et al. |
| 2003/0099277 A1 | 5/2003 | Bellifemine |
| 2003/0171655 A1 | 9/2003 | Newman et al. |
| 2004/0124359 A1 | 7/2004 | Hamrelius et al. |
| 2005/0117624 A1 | 6/2005 | Hollander et al. |
| 2006/0222048 A1 | 10/2006 | Pompei |
| 2007/0055171 A1 | 3/2007 | Fraden |
| 2007/0189358 A1 | 8/2007 | Lane et al. |
| 2008/0175301 A1 | 7/2008 | Chen |
| 2009/0182526 A1 | 7/2009 | Quinn et al. |
| 2009/0299682 A1 | 12/2009 | Yarden et al. |
| 2011/0194585 A1 | 8/2011 | Shrivastava |
| 2012/0143079 A1 | 6/2012 | Lia et al. |
| 2012/0253205 A1 | 10/2012 | Cho et al. |
| 2014/0046192 A1 | 2/2014 | Mullin et al. |

FOREIGN PATENT DOCUMENTS

| | | |
|---|---|---|
| EP | 0446788 A1 | 9/1991 |
| EP | 0875197 | 11/1998 |
| GB | 2311368 | 9/1997 |
| JP | 01124727 | 5/1989 |
| JP | 2001054505 | 2/2001 |
| JP | 2011072639 | 4/2011 |
| WO | WO8606163 | 10/1986 |
| WO | WO0016046 A2 | 3/2000 |
| WO | WO0016047 | 3/2000 |
| WO | WO2012067282 A1 | 5/2012 |
| WO | WO2012067422 A2 | 5/2012 |
| WO | WO2012067423 A2 | 5/2012 |

OTHER PUBLICATIONS

Cardone et al., "Temperature maps measurements on 30 surfaces with infrared thermography", Exp Fluids 52:375-385, published online Nov. 24, 2011.

Watmough et al., "The Thermal Scanning of a Curved Isohermal Surface: Implications for Clinical Thermography", Phys. Med. Bioi. 1970, vol. 15, No. 1,1-8.

You et al., "Fusion of Vision and Gyro Tracking for Robust Augmented Reality Registration", Proceedings of the Virtual Reality 2001 Conference (VR'01 ), IEEE.

Coret et al., "Simulation Study of View Angle Effects on Thermal Infrared Measurements Over Heterogeneous Surfaces" IEEE Transactions on Geoscience and Remote Sensing, vol. 42, No. 3, 2004.

Baker et al., "Effects on the Variation of Angle of Incidence and Temperature on Infrared Filter Characteristics" Applied Optics, vol. 6, No. 8, 1967.

Combined electronic contact and contact less thermometer Source: http://www.naasltd.com/online-shop/featured-products/combined-electronic-contact-and-contactless-thermometer; Accessed Date: Oct. 12, 2011 and Jun. 17, 2013.

Fluke 566 IR-Thermom Source: http://shop.conrad-uk.com/tools/measurement/environmentalmeasurement/temperature-measurement/ir-thermometers/122370.html; Accessed Date: Oct. 12, 2011 and Jun. 17, 2013.

"New Fluke SmartView 2.0 thermal imaging software features industry-first 3D capability", retrieved on Sep. 19, 2013 at <<http://www.fluke.com/fluke/usen/about?press/smartview%202.0%20thermal%20imaging%20software.htm>>, Fluke, Published Oct. 16, 2008, 2 pages.

Foote, et al., "Progress Towards High-Performance Thermopile Imaging Arrays", Infrared Technology and Applications XXVII, Proceedings of SPIE, vol. 4369 (2001 ). pp. 350-354.

International Search Report and the Written Opinion of the International Searching Authority. or the Declaration, Mailed Nov. 7, 2013 (14 pages).

Lee et al., "Low-Cost Dual Rotating Infrared Sensory for Mobile Robot Swarm Applications", IEEE Transactions on Industrial Informatics, vol. 7, No. 2, 2011, pp. 277-286.

Ng, et al., "Analysis of IR thermal imager for mass blind fever screening", Microvascular Research 68 (2004), pp. 104-109.

Office Action for U.S. Appl. No. 13/569,867, mailed on Sep. 27, 2013, Matthew D. Mullin, "Temperature Measurement System", 18 pages.

Thermometer Reviews and Buying Guide Source: http://www.galttech.com/research/health/bestthermometer-taking-a-temperature.php; Accessed Date: Oct. 12, 2011 and Jun. 17, 2013.

Brunelli, "Template Matching Techniques in Computer Vision: Theory and Practice", Chapter 1, John Wiley & Sons, Ltd, 2009, pp. 1-8.

Lenhardt et al., "Estimation of Mean Body Temperature from Mean Skin and Core Temperature", retrieved on Aug. 7, 2015 at http://anesthesiology.pubs.asahq.org/pdfaccess.ashx?url=/data/Journals/JASA/931044/, Anesthesiology, V. 105, No. 6, 2006, 5 pages.

Office action for U.S. Appl. No. 13/569,867, mailed on Sep. 1, 2015, Mullin et al., "Temperature Measurement System", 23 pages.

* cited by examiner

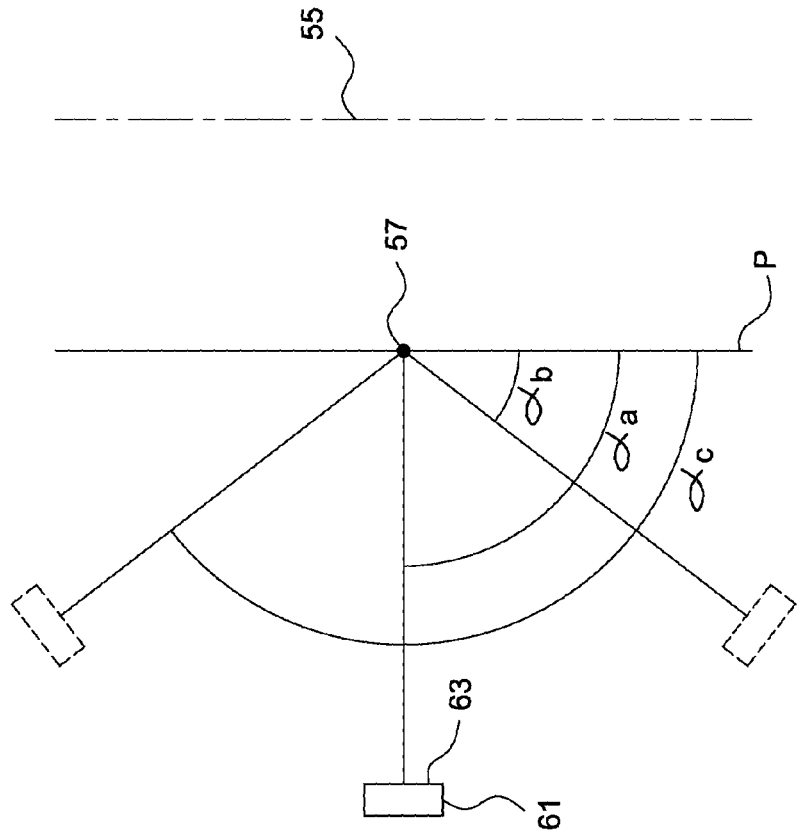
FIG. 6
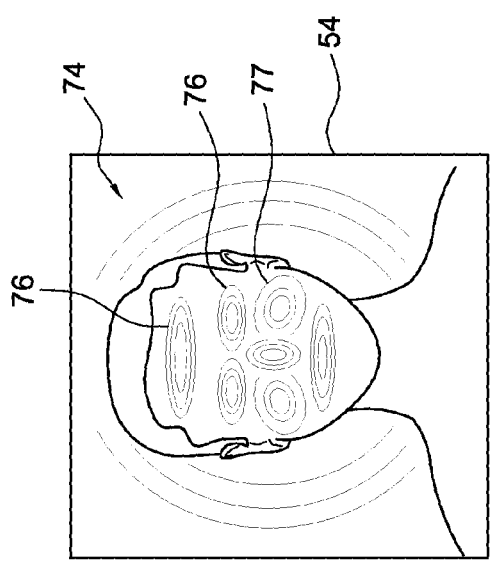
FIG. 5
FIG. 7

TEMPERATURE MEASUREMENT SYSTEM

CROSS-REFERENCE TO RELATED APPLICATION

This application is a continuation of pending U.S. patent application Ser. No. 13/569,867, filed Aug. 8, 2012, the entire disclosure of which is hereby incorporated herein by reference.

FIELD OF THE INVENTION

The present disclosure relates to systems and methods for temperature determination and, in particular, to systems and methods for determining a patient's core temperature.

BACKGROUND OF THE INVENTION

Temperature is an important vital sign in patient evaluation. Physicians commonly use a variety of methods for determining patient temperature including, for example, obtaining temperature measurements with a thermometer. While thermometers utilizing mercury have been in existence for many years, modern thermometers typically employ one or more electronic sensors configured to measure patient temperature. Such sensors may take one or more measurements over a relatively short period of time. Based on these measurements, the thermometer may generate an estimated internal and/or core temperature of the patient. In generating this estimated core temperature, it is common practice to insert at least a portion of the thermometer into a disposable cover prior to taking temperature measurements. The cover may overlay the electronic temperature sensor of the thermometer, and may protect the sensor from contamination during use.

Determining core temperature in this way, however, can be problematic in certain situations. For example, despite the use of such disposable covers, harmful germs and other contaminants can be carried by the thermometer itself, from patient to patient, due to the close proximity between the patient and the thermometer when taking the temperature measurement. As a result, non-contact thermometers have become increasingly popular among healthcare professionals. Such non-contact thermometers typically employ a sensing element configured to measure the temperature of, for example, the patient's forehead, temple, and/or other external body surfaces without contacting these surfaces, and to estimate the patient's core temperature based on such measurements. However, the temperature of these external body surfaces does not often correlate well to temperature measurements taken at traditional measurement sites such as the oral cavity, rectal cavity, axilla area, or tympanic membrane. Thus, the core temperature estimates made by such non-contact devices are not as accurate as core temperature estimates made by traditional contact-based thermometers. The accuracy of measurements taken with existing non-contact thermometers is highly dependent upon the distance and alignment of the device relative to the external body surface. Thus, measurements taken with such devices are prone to significant error and, by themselves, such devices are not highly reliable as a means of patient evaluation.

The exemplary embodiments of the present disclosure are directed toward overcoming the deficiencies described above.

SUMMARY

In an exemplary embodiment of the present disclosure, a method of determining a temperature of a patient includes measuring a first temperature of the patient with a temperature device without contacting the patient with the device, and measuring a second temperature of the patient by contacting a measurement site of the patient with the device. The method also includes determining a temperature value indicative of a core temperature of the patient based on the first and second temperatures.

In another exemplary embodiment of the present disclosure, a temperature measurement system includes a temperature device including a first temperature sensor configured to determine a first temperature of a patient without contacting the patient with the device. The temperature device also includes a second temperature sensor configured to determine a second temperature of the patient by contacting a measurement site of the patient with a component of the system. The temperature device further includes a controller associated with the device. The controller is configured to receive signals indicative of the first and second temperatures from the first and second temperature sensors, and to determine a temperature value indicative of a core temperature of the patient based the first and second temperatures.

In a further exemplary embodiment of the present disclosure, a method of determining a temperature of a patient with a temperature device includes selecting between at least three operating modes of the temperature device. In a first operating mode, the temperature device is configured to measure a first temperature of the patient without contacting the patient with the device and determine a first temperature value indicative of a core temperature of the patient based on the first temperature. In a second operating mode, the temperature device is configured to measure a second temperature of the patient by contacting a measurement site of the patient with the device and determine a second temperature value indicative of the core temperature of the patient based on the second temperature. In a third operating mode, the temperature device is configured to measure the first and second temperatures of the patient, and determine a third temperature value indicative of the core temperature of the patient based on the first and second temperatures. In such a method, in the first operating mode, the first temperature value is determined without regard to the second temperature. Additionally, in the second operating mode, the second temperature value is determined without regard to the first temperature.

In still another exemplary embodiment of the present disclosure, a method of determining a temperature of a patient with a temperature device includes determining an alignment parameter associated with a position of the device relative to the patient. In such a method, the alignment parameter is at least one of a distance between the device and the patient, and an angle formed between the device and a plane substantially defined by an outer surface of the patient. Such an exemplary method also includes measuring a temperature of the patient with a temperature sensor of the temperature device without contacting the patient with the device. In such a method, the temperature sensor is an array of infrared sensing elements, and measuring the temperature includes focusing at least one of the sensing elements on a location on the outer surface. Such a method also includes determining a temperature value indicative of a core temperature of the patient based on the temperature.

BRIEF DESCRIPTION OF THE DRAWINGS

FIG. 5 is an exemplary schematic diagram illustrating various positions of a sensor relative to a plane.

FIG. 6 is another exemplary schematic diagram illustrating various positions of a sensor relative to a plane.

FIG. 7 illustrates an exemplary thermal image according to an embodiment of the present disclosure.

DETAILED DESCRIPTION

Figure 1:
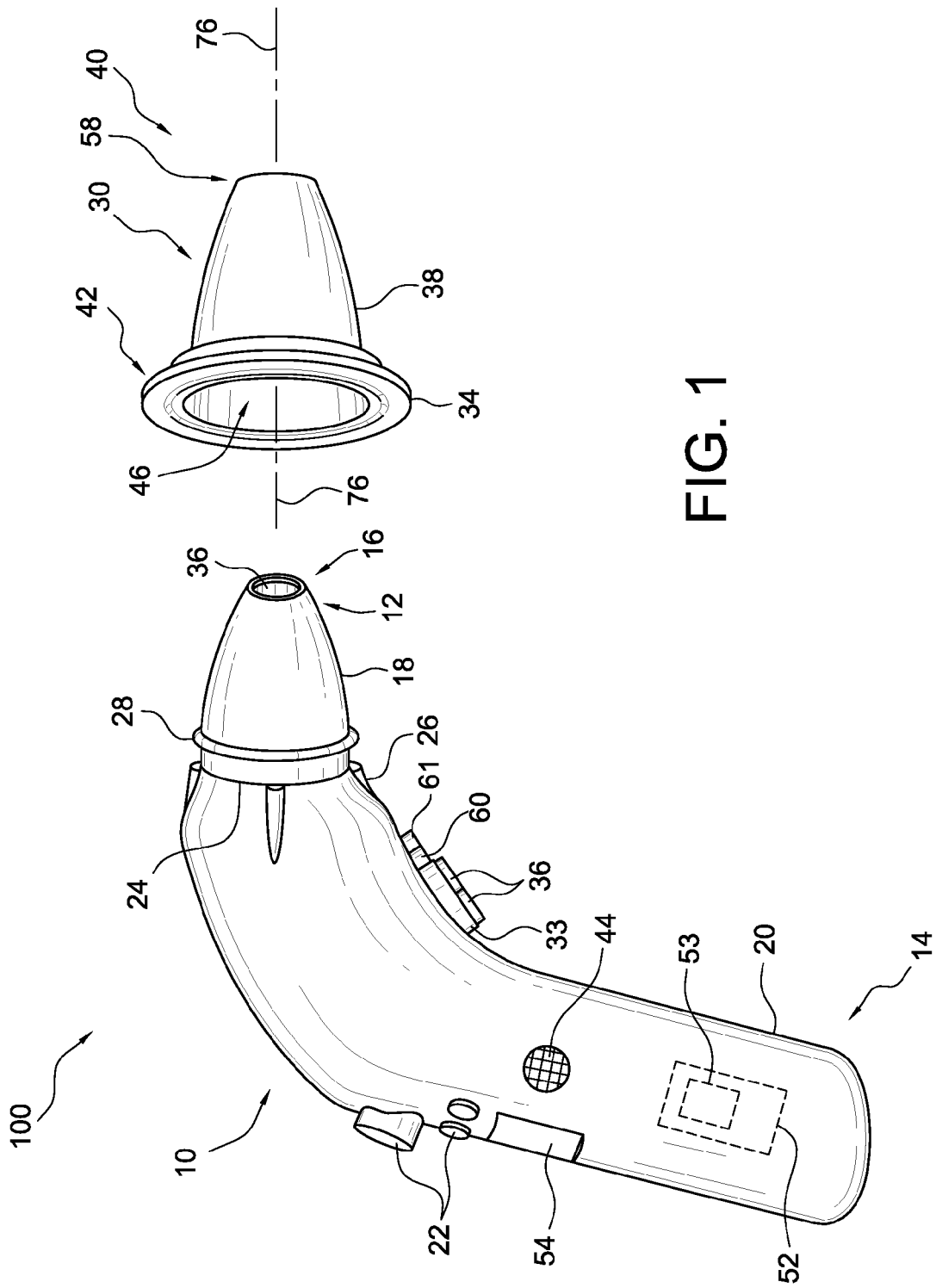
FIG. 1 illustrates a temperature measurement system according to an exemplary embodiment of the present disclosure.
Figure 8:
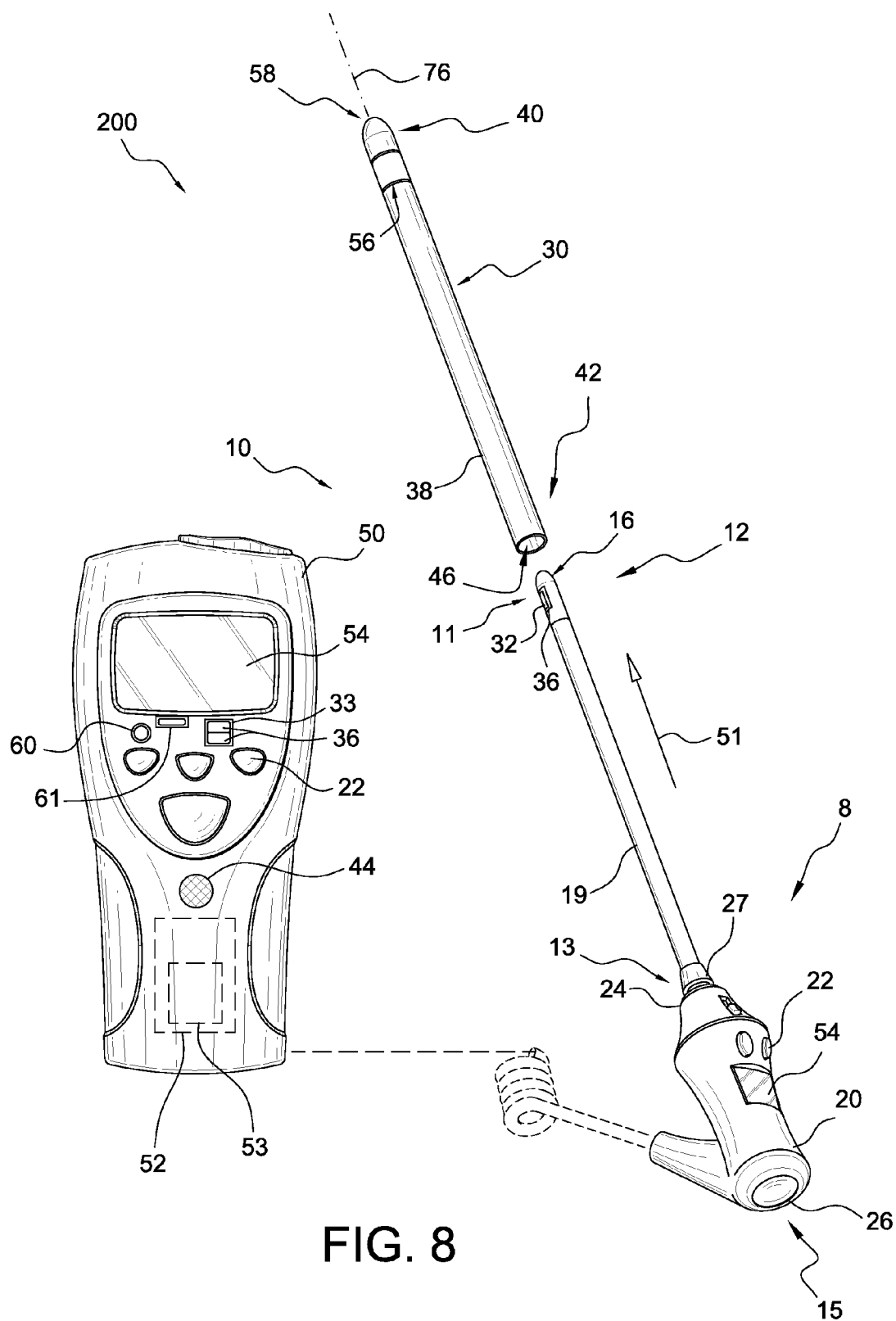
FIG. 8 illustrates a temperature measurement system according to another exemplary embodiment of the present disclosure.

FIG. 1 illustrates a first exemplary temperature measurement system 100 of the present disclosure including a temperature device 10 and a corresponding probe cover 30. FIG. 8 illustrates a second exemplary temperature system 200 of the present disclosure including a temperature device 10. The temperature device 10 of the temperature measurement system 200 includes a probe 8 and a handpiece 50 operably connected to the probe 8. The temperature measurement system 200 also includes a probe cover 30 corresponding to the probe 8. Whenever possible, like item numbers will be used throughout this disclosure to identify like components of the temperature systems 100, 200. Additionally, as will be described herein, implementation of the present technology in the temperature devices 10 of systems 100, 200 is merely exemplary. The disclosed technology may be applicable to any other medical device that may use a cover, sheath, and/or other structure to protect the device from contaminants present on a surface or in a cavity of the body. Such medical devices may include, for example, probes, endoscopes, speculums, and/or other like devices where the characteristics of the cover, sheath, and/or other like structures impact the accuracy or precision of data gathered or measurements taken by the medical device.

As shown in FIG. 1, the temperature device 10 of exemplary system 100 may include, for example, a head 18 connected to a handle 20. The head 18 may define a distal end 12 of the temperature device 10, and the handle 20 may define a proximal end 14 of the device 10. The head 18 may include an atraumatic tip 16 disposed at the distal end 12. The tip 16 may be sufficiently rounded and/or otherwise configured so as not to cause injury to a patient upon contact with a body surface or at least partial insertion of the head 18 within one or more body cavities of the patient. In an exemplary embodiment in which the temperature device 10 is utilized to measure, calculate, estimate and/or otherwise determine a core temperature of the patient, it is understood that such body cavities may include the ear, oral cavity, rectal cavity, axilla area, and/or other known body cavities from which temperature may be sensed. Collectively, such body cavities and/or body surfaces may be referred to herein as "patient measurement sites." In further exemplary embodiments, such patient measurement sites may also include a forehead of the patient and/or any other known or easily accessible outer surface of the patient. Such outer surfaces may include the patient's skin or eyes.

The head 18 and/or the handle 20 may be made from any material and/or combinations of materials commonly used in medical and/or examination procedures. Such materials may include, for example, plastics, polymers, composites, stainless steel, alloys, and/or any other like materials. Such materials may be suitable for repeated use and/or repeated sanitation. Accordingly, in an exemplary embodiment of the present disclosure, the temperature device 10 and/or its components may be substantially waterproof. One or more waterproof seals may be included and/or otherwise utilized with components of the temperature device 10 to facilitate such repeated sanitation and/or use.

Alternatively, in the exemplary embodiment shown in FIG. 8, the temperature device 10 may include, for example, a shaft 19 extending from a handle 20 of the probe 8. In the embodiment of FIG. 8, the atraumatic tip 16 may be disposed at a distal end 12 of the shaft 19, and the tip 16 may be sufficiently rounded and/or otherwise configured so as not to cause injury to a patient upon contact with and/or at least partial insertion of the shaft 19 within one or more of the patient measurement sites described herein. The shaft 19 and/or the handle 20 of FIG. 8 may be made from any of the materials described above with respect to the head 18 and handle 20 illustrated in FIG. 1.

The handle 20 shown in FIGS. 1 and 8 may include one or more operator interfaces 22. Such operator interfaces 22 may be configured to assist in performing one or more functions of the temperature device 10. For example, the operator interfaces 22 may comprise any combination of switches, buttons, levers, knobs, dials, keys, and/or other like components configured to activate, deactivate, manipulate, and/or otherwise control components of the temperature device 10. Such operator interfaces 22 may, for example, assist the user in toggling through and/or selecting one or more modes of operation of the temperature device 10, enabling and/or disabling one or more sensors, alarms, and/or signals associated with operation of the device 10, initiating a single substantially instantaneous temperature calculation, initiating a substantially continuous and/or repeating temperature calculation, and/or other like modes, functions, or operations.

In the exemplary embodiment shown in FIG. 1, at least one of the operator interfaces 22 may be operably connected to an ejector mechanism 26 disposed proximate a base 24 of the head 18. At least a portion of the temperature device 10 may be inserted into the probe cover 30 before and/or during use, and such an ejector mechanism 26 may be configured to assist in removing the probe cover 30 from the temperature device 10. For example, the ejector mechanism 26 may comprise one or more extensions, flanges, clamps, hooks, shoulders, arms, tabs, rings, and/or other like structures configured to assist in ejecting the probe cover 30 from the base 24 of the head 18 after use. In an exemplary embodiment, one or more such ejector mechanisms 26 may be movable with respect to the base 24 and/or the head 18. In such exemplary embodiments, the ejector mechanisms 26 may be movable in, for example, a path substantially parallel to the head 18. In additional exemplary embodiments, the ejector mechanisms 26 may be movable in an arcuate path relative to the head 18. Movement of the ejector mechanisms 26 may assist in bending, flexing, and/or otherwise deforming at least a portion of the probe cover 30. For example, the ejector mechanisms 26 may be movable along one or more camming surfaces and/or other like external surfaces of the probe cover 30, and such movement may assist in flexing at least a portion of the probe cover 30.

Such flexing may ultimately overcome a retention force provided by one or more retention components 28 of the temperature device 10 and/or by one or more retention components 80 (FIG. 2) of the probe cover 30, thereby releasing the probe cover 30 from the temperature device 10. For example, as shown in FIG. 1, a typical retention component 28 of the temperature device 10 may include a raised ring, flange, shoulder, and/or other like structure. Such a retention component 28 may extend partially or completely around, for example, a proximal portion of the head 18, and in exemplary embodiments, one or more such retention components 28 may be disposed about the head 18. Regardless of its form, such a retention component 28 may be configured to releasably mate with a corresponding retention component 80 (FIG. 2) of the probe cover 30 to assist in releasably coupling the probe cover 30 to the temperature device 10.

Alternatively, in the exemplary embodiment illustrated in FIG. 8, an ejector mechanism 26 may be disposed at a proximal end 15 of the probe 8. In such an exemplary embodiment, at least a portion of the temperature device 10, such as the shaft 19, may be inserted into a probe cover 30 before and/or during use, and such an ejector mechanism 26 may be configured to assist in removing the probe cover 30 from the temperature device 10. For example, actuating the ejector mechanism 26 may extend the shaft 19, in the direction of arrow 51, a desired distance from a base 24 formed at a proximal end 13 of the shaft 19. Extending the shaft 19 in this way may eject and/or otherwise remove the probe cover 30 from the shaft 19. In particular, extending the shaft 19 in the direction of arrow 51 may overcome a retention force provided by one or more shoulders, rings, tabs, extensions, and/or other like stationary retention components 27 of the temperature device 10. Such stationary retention components 27 may be disposed, for example, proximate the base 24.

In exemplary embodiments, one or more operator interfaces 22 may be operably connected to at least one sensor 32 (FIGS. 2 and 8) of the temperature device 10. In the exemplary embodiment shown in FIG. 2, the sensor 32 may be embedded within and/or otherwise formed integrally with the head 18 and/or the handle 20. In such exemplary embodiments, it is understood that the sensor 32 may be electrically, operably, and/or otherwise connected to the operator interfaces 22 and/or other components of the temperature device 10 via known electrical connections. Alternatively, as shown in FIG. 8, the sensor 32 may be embedded within and/or otherwise formed integrally with the shaft 19. In such exemplary embodiments, the sensor 32 may be disposed, for example, at a distal end 11 of the shaft 19, such as proximate the tip 16. As will be described in greater detail below, in each of the exemplary embodiments disclosed herein, the sensor 32 may be operably, controllably, electrically, and/or otherwise connected to a controller 52 disposed internal or external to the temperature device 10. In such an exemplary embodiment, the controller 52 may be configured to assist in estimating a core temperature of a patient based on signals and/or other inputs from one or more of the sensors described herein.

In an exemplary embodiment, the sensor 32 may be configured to sense one or more vital signs or physical characteristics of a patient such as, for example, temperature, blood pressure, and the like. In an exemplary embodiment, the sensor 32 may comprise a temperature sensor, such as a thermopile, thermocouple, and/or thermistor, configured to sense a temperature associated with the patient. For example, such a sensor 32 may be configured to sense a temperature of the patient measurement site into which a portion of the temperature device 10 has been inserted and/or with which the temperature device 10 has otherwise been placed in contact. It is understood that in exemplary embodiments, measuring a temperature of the patient by contacting a patient measurement site with the temperature device 10 may include contacting the patient measurement site with the temperature device 10 while a probe cover 30 is disposed on the head 18 or shaft 19 thereof. In such exemplary embodiments, contact between the temperature device 10 and the patient measurement site may include contact between the probe cover 30 and the patient measurement site. For example, in embodiments in which the patient measurement site comprises the patient's ear, a portion of the head 18 of the temperature device 10 shown in FIG. 1 may be inserted into the ear such that a temperature associated with, for example, the tympanic membrane of the patient may be determined. In such embodiments, a probe cover 30 of the temperature device 10 may actually contact the ear and/or portions of the ear canal while the sensor 32 measures the temperature associated with the tympanic membrane. Alternatively, in embodiments in which the patient measurement site comprises the patient's oral cavity, a portion of the shaft 19 of the temperature device 10 shown in FIG. 8 may be inserted into the patient's mouth such that a temperature measurement may be taken. In such embodiments, a probe cover 30 of the temperature device 10 may actually contact a surface of the mouth beneath the tongue, and/or other portions of the oral cavity, while the sensor 32 measures an associated temperature.

In exemplary embodiments, the sensor 32 may comprise an infrared temperature sensor such as, for example, a thermopile and/or other like infrared-based temperature sensing components. Such a sensor 32 may be configured to convert thermal energy into electrical energy, and may comprise two or more thermocouples connected in series or in parallel. Such components may be configured to generate an output voltage proportional to a local temperature difference and/or temperature gradient. In an exemplary embodiment in which the sensor 32 comprises at least one thermopile, the temperature device 10 may comprise, for example, an infrared temperature probe and/or other like infrared thermometer. In such embodiments, the sensor 32 may be configured to receive and/or emit radiation 62 (FIG. 2), such as thermal and/or infrared radiation. For example, the sensor 32 may be configured to sense, detect, collect, and/or otherwise receive radiation 62 emitted by the patient. Such radiation 62 may be emitted by, for example, the tympanic membrane and/or any of the patient measurement sites described herein. In such embodiments, the sensor 32 may be configured to collect the radiation 62, and to send a signal to the controller 52 indicative of the collected radiation 62. The controller 52 may utilize the received signal for any number of known functions. For example, the controller 52 may be configured to estimate, infer, calculate, and/or otherwise determine a core temperature of the patient based on the signal and/or one or more additional inputs.

The sensor 32 may be configured to collect radiation 62 that is reflected, reemitted, and/or otherwise returned to the sensor 32. For example, at least a portion of such radiation 62 may reflect off of the tympanic membrane and/or may be absorbed and reemitted by the membrane. In such embodiments, the sensor 32 may be configured to collect the reflected and/or reemitted radiation 62, and to send a signal to the controller 52 indicative of the collected radiation 62.

The temperature device 10 may additionally include at least one window, lens, and/or other like optical component 36 positioned proximate the sensor 32. For example, such an optical component 36 may be disposed substantially flush and/or coplanar with the outer surface of the head 18 shown in FIGS. 1 and 2. Such optical components 36 may be disposed, for example, at the tip 16 of the temperature device 10, and may be configured to assist in, for example, focusing, directing, and/or otherwise transmitting radiation 62 to the sensor 32 for collection. In additional exemplary embodiments, such optical components 36 may assist in focusing, directing, and/or otherwise transmitting radiation 62 emitted by the sensor 32. Such optical components 36 may also assist in protecting the thermopile, thermocouple, thermistor, and/or other sensor components during use of the temperature device 10, and may assist in forming a substantially fluid tight compartment 82 (FIG. 2) within the head 18 to protect sensor components from contact with bodily fluids, cleaning solutions, and/or other liquids. It is understood that such optical components 36 may be substantially transparent to assist in the transmission of infrared and/or other types of radiation 62. In exemplary embodiments, the optical components 36 may comprise one or more convergent, collimating, and/or divergent lenses.

It is understood that in the exemplary embodiment illustrated in FIG. 8, the sensor 32 may comprise a thermopile, thermocouple, a thermistor, and/or any of the other temperature sensors described above, configured to sense a temperature associated with the patient. The sensor 32 may be configured to sense a temperature of the patient measurement site into which the shaft 19 and/or other portion of the temperature device 10 has been inserted, and/or with which the shaft 19 and/or other portion of the temperature device 10 has otherwise been placed in contact. In the exemplary embodiment shown in FIG. 8, one or more optical components 36 may be disposed substantially flush and/or coplanar with the outer surface of the shaft 19. In an exemplary embodiment in which the shaft 19 is substantially cylindrical, such optical components 36 may be substantially curved so as to match the radius of curvature of the shaft 19. Such optical components 36 may assist in, for example, focusing and/or transmitting infrared radiation between a thermopile of the sensor 32 and the patient measurement site. Such optical components 36 may also assist in protecting the thermopile, thermocouple, thermistor, and/or other sensor components during use of the temperature device 10, and may assist in forming a substantially fluid tight compartment (not shown) within the shaft 19 so as to protect sensor components from contact with bodily fluids, cleaning solutions, and/or other liquids. It is understood that such optical components 36 may be substantially transparent to assist in the transmission of radiation to and/or from the sensor 32. Such optical components 36 may also be highly electrically-transmissive and may have a negligible effect on, for example, an electric field generated by the sensor 32.

Figure 3:
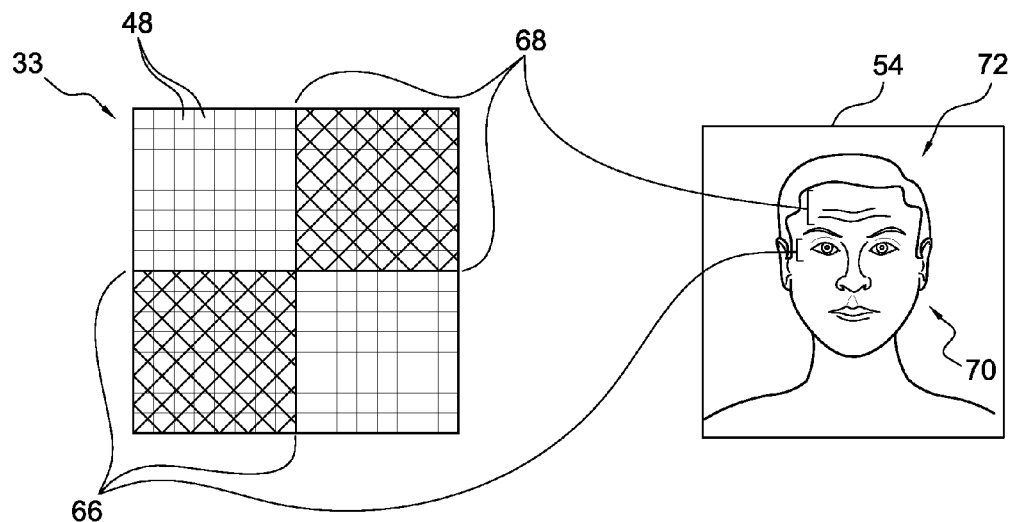
FIG. 3 illustrates an exemplary sensor and an exemplary display of the present disclosure.

In exemplary embodiments, the temperature device 10 may include one or more additional sensors configured to assist in determining one or more physical characteristics of the patient. In an exemplary embodiment, at least one such sensor 33 may be the same type of sensor described above with respect to sensor 32. For example, the sensor 33 may comprise any type of sensor, such as a thermocouple and/or thermistor, configured to sense a temperature associated with the patient. In an additional exemplary embodiment, the sensor 33 may comprise an infrared temperature sensor such as, for example, a thermopile and/or other like infrared-based sensor. As shown in FIG. 3, in still further embodiments, the sensor 33 may comprise an array of pixels and/or other like sensing elements 48 configured to determine a temperature of the patient. In exemplary embodiments, an array of sensing elements 48 may include one or more such sensing elements 48 configured to sense a temperature of an outer surface 70 of the patient. As noted above, such outer surfaces 70 may include, for example, a skin surface such as the face, an eye, and/or any other like outer body surface of the patient. Such sensors 33 may be configured to determine a temperature of the outer surface 70 without contacting the patient with the temperature device 10.

In exemplary embodiments, the one or more sensing elements 48 of sensor 33 may be configured to determine more than one temperature of the outer surface 70. For example, an array of sensing elements 48 included in sensor 33 may be configured to sense, measure, observe, read, and/or otherwise survey the outer surface 70 from one or more locations relative to the patient. In such embodiments, the controller 54 and/or the sensing elements 48 of sensor 33 may be configured to generate a two or three-dimensional temperature measurement of the patient and, in particular, of the outer surface 70. For example, a user of the temperature device 10 illustrated in FIGS. 1 and 4 may rotate the temperature device 10 about one or more axes 55, 57 passing substantially through and/or otherwise substantially defined by the patient while sensing a temperature of the outer surface 70 with the sensor 33. It is understood that, in further exemplary embodiments, one or more of the axes 55, 57 may be substantially defined by the temperature device 10. Alternatively, a user of the temperature device 10 illustrated in FIGS. 8 and 9 may rotate the handpiece 50 about one or more of the axes 55, 57 while sensing a temperature of the outer surface 70 with the sensor 33. In the exemplary embodiments shown in FIGS. 8 and 9, the sensor 33 may be disposed on the handpiece 50, while in further exemplary embodiments of the system 200, the sensor 33 may be disposed on, for example, the handle 20 or the shaft 19 of the probe 8. In such further exemplary embodiments of the system 200, the user may rotate the probe 8 about one or more of the axes 55, 57 while sensing a temperature of the outer surface 70 with the sensor 33. It is understood that movement of the handpiece 50 and/or the probe 8 relative to the axes 55, 57 and/or otherwise relative to the patient may comprise movement of the temperature device 10 shown in FIGS. 8 and 9.

Figure 4:
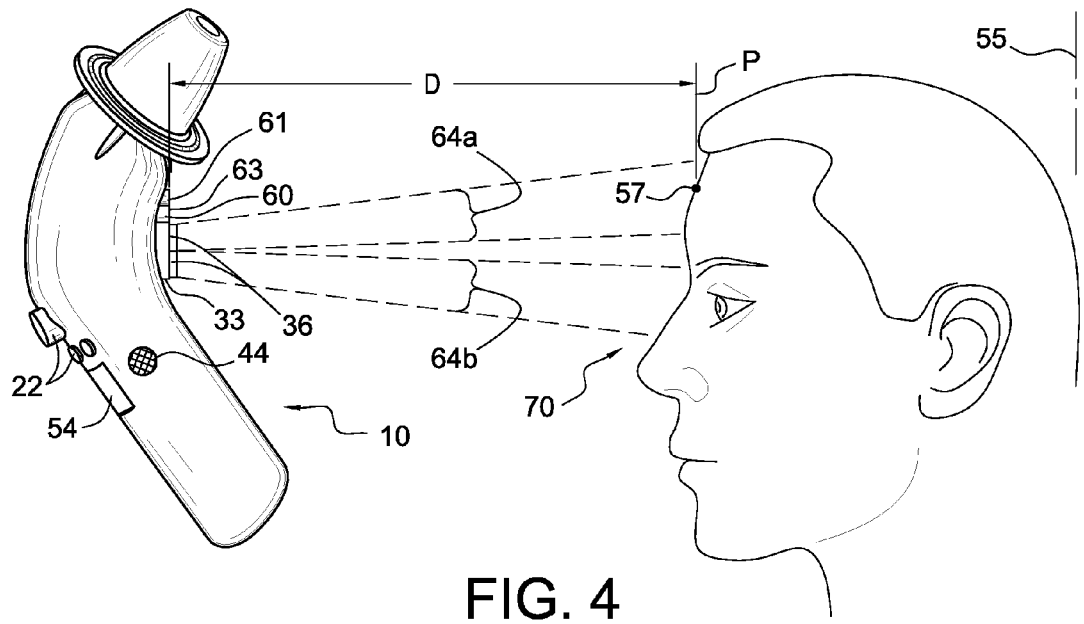
FIG. 4 is another exemplary view of the temperature measurement system shown in FIG. 1.

In exemplary embodiments, the axis 55, may be substantially collinear with, for example, the spine of the patient and/or any other like bone or bone structure. In such exemplary embodiments, the axis 57 may be substantially orthogonal to the axis 55. As shown in FIG. 4, in exemplary embodiments, the axis 57 may be substantially defined by an outer surface 70 of the patient such as, for example, the patient's forehead. In exemplary embodiments, in which the axis 55 is substantially defined by the patient's spine and the axis 57 is substantially defined by an outer surface 70, the axis 55 may be spaced from the axis 57. It is further understood that the axes 55, 57 may be disposed in and/or otherwise defined by one or more planes. For example, a sagital, coronal, parasagital, and/or paracoronal plane of the patient may include one or more of the axes 55, 57, and in further exemplary embodiments, the axis 55 may be formed by the intersection of the sagital and coronal planes. Likewise, the axis 57 may be formed by the intersection of the coronal plane with a transverse plane of the patient passing through, for example, the forehead.

Relative movement between the temperature device 10 and the patient, such as movement of the temperature device 10 and/or the sensor 33 about, along, substantially parallel to, substantially perpendicular to, at an angle to, and/or otherwise relative to one or more of the axes 55, 57, may assist in measuring the temperature of the outer surface 70 from a plurality of different points, angles, locations, and/or positions. Various temperature measurements taken during such relative movement may assist the temperature device 10 in generating, for example, the three-dimensional temperature measurement of the patient mentioned above. Such an exemplary three-dimensional temperature measurement will be described in greater detail below with respect to FIG. 7. Such relative movement may also assist in measuring the temperature of more than one location on the outer surface 70. For example, in embodiments in which the outer surface 70 comprises the patient's face, such locations may include the patient's forehead, eyes, nose, sinus region, temple, lips, and/or other anatomical structures or patient measurement sites found on the face. Multiple temperature measurements obtained by moving the array of sensing elements 48 of sensor 33 relative to the outer surface 70 may be directed to the controller 52. The controller 52 may use such measurements as inputs into one or more algorithms, control maps, and/or look-up tables to assist in generating, for example, the three-dimensional temperature measurement of the patient.

The sensor 33 may include any of the optical components 36 described above with respect to the sensor 32. For example, at least one window, lens, and/or other like optical component 36 may be positioned proximate the sensor 33, and may be configured to assist in, for example, focusing, directing, and/or otherwise transmitting radiation 62 to the sensor 33 for collection. Such optical components 36 may be substantially transparent to assist in the transmission of infrared and/or other types of radiation to the sensor 33, and in exemplary embodiments, the optical components 36 may comprise one or more convergent, collimating, and/or divergent lenses. Such optical components 36 may be configured to assist in, for example, focusing one or more sensing elements 48 of the sensor 33 on one or more respective locations associated with the outer surface 70 of the patient. For example, the optical components 36 may be configured to focus a first plurality 66 (FIG. 3) of sensing elements 48 of a pixel array associated with the sensor 33 on a first location of the outer surface 70. The optical components 36 may also be configured to focus a second plurality 68 of sensing elements 48 of the pixel array on a second location of the outer surface 70. For example, as illustrated in FIG. 3, if such an exemplary outer surface 70 comprises a face of the patient, the first location may include at least one of the patient's eyes while the second location may include the patient's forehead. It is understood that the locations described with respect to FIG. 3 are merely exemplary. Moreover, in exemplary embodiments the first, second, and/or additional locations on the outer surface 70 may be substantially simultaneously focused upon by the optical components 36 and/or the sensing elements 48. By focusing, for example, an array of pixels and/or other sensing elements 48 of the sensor 33 in this way, exemplary embodiments of the temperature device 10 may be configured to only use temperature measurements and/or other inputs corresponding to the locations on the outer surface 70 that are brought within a field of view 64a, 64b (FIGS. 4 and 9) of the respective sensing elements 48.

In further exemplary embodiments, the temperature device 10 may include one or more additional components such as, for example, a camera or other like imaging device 60. Such imaging devices 60 may be configured to capture digital, thermal, and/or other like images of the patient. For example, the imaging device 60 may comprise a digital camera operably connected to the controller 52 and configured to capture an image of the outer surface 70 and/or other portions of the patient. Alternatively, and/or in addition, the imaging device 60 may be configured to collect thermal, infrared, and/or other radiation 62 emitted by the patient, and to form a thermal image of the patient using and/or based on the collected radiation 62. In such exemplary embodiments, the imaging device 60 may be configured to form a thermal image of the patient independently or in combination with the sensing elements 48 of the sensor 33.

In further exemplary embodiments, the controller 52 may include components such as an image processor 53 (FIGS. 1 and 8) configured to receive signals and/or other inputs from the imaging device 60. The image processor 53 may be configured to assist in forming an image of the patient based on such inputs. For example, in embodiments in which the imaging device 60 comprises a digital camera, the image processor 53 may receive signals and/or other inputs from the imaging device 60, and may assist in forming a visual image 72 of the patient based on such inputs. As shown in FIG. 3, such a visual image 72 may be illustrated on a display 54 of the temperature device 10. In the exemplary embodiment shown in FIG. 8, such a display 54 may be included as a component of the probe 8 and/or the handpiece 50.

Alternatively, in embodiments in which the imaging device 60 is configured to collect thermal, infrared, and/or other radiation 62 emitted by the patient, the image processor 53 may receive signals and/or other inputs from the imaging device 60 indicative of such collected radiation 62. In such embodiments, the image processor 53 may assist in forming a thermal image 74 of the patient based on such inputs. As shown in FIG. 7, the thermal image 74 may be illustrated on the display 54, and such a thermal image 74 may comprise a two or three-dimensional image, temperature gradient, and/or temperature profile of the patient as described above.

In exemplary embodiments, one or more of the images 72, 74 described herein may be used to correlate one or more sensing elements 48 of the sensor 33 with one or more respective locations associated with the outer surface 70 of the patient. For example, based on inputs received from the imaging device 60, the image processor 53 and/or other components of the temperature device 10, the controller 52 may employ one or more algorithms, image recognition programs, or software routines to correlate the first plurality 66 of sensing elements 48 with the first location on the outer surface 70. Using such algorithms and/or software routines, the controller 52 may also correlate the second plurality 68 of sensing elements 48 with a second location of the outer surface 70. For example, as shown in FIG. 3, if such an exemplary image 72 of the outer surface 70 illustrates a face of the patient, the first plurality 66 of sensing elements 48 may be correlated with a first location including at least one of the patient's eyes, while the second plurality 68 of sensing elements 48 may be correlated with a second location including the patient's forehead.

In such correlation processes, one or more sensing elements 48 of the sensor 33 may be controlled and/or otherwise directed by the controller 52 to only measure temperature associated with the correlated location on the outer surface 70 and/or to ignore temperature associated with locations on the outer surface 70 other than the correlated location. For example, through such a correlation process, one or more of the sensing elements 48 may remain inactive until a correlated and/or otherwise recognized location on the outer surface 70 is brought within the field of view 64a, 64b (FIGS. 4 and 9) of the one or more sensing elements 48.

In further exemplary embodiments, the controller 52 may be configured to compare, for example, inputs correlated to different locations on the outer surface 70, and to determine one or more physical characteristics of the patient based on the comparison. For example, at least one of the sensing elements 48 may be correlated to a first location on the outer surface 70 illustrated in an image 72 of the patient. In such exemplary embodiments, at least one sensing element 48 may be correlated with, for example, a sinus region and/or other anatomical structures of the patient illustrated in the image 72. The sensing element 48 may be configured to determine a temperature of the sinus region as described above. In such an exemplary embodiment, at least one additional sensing element 48 may be correlated to a second location on the outer surface 70 illustrated in the image 72 different than the first location. For example, the additional sensing element 48 may be correlated with a forehead and/or other anatomical structure of the patient illustrated in the image 72. The additional sensing element 48 may be configured to determine a temperature of the forehead. Both sensing elements 48 may send signals indicative of the respective determined temperatures to the controller 52, and the controller 52 may compare the two temperatures with respect to the locations on the outer surface 70 from which the respective temperatures were obtained. In exemplary embodiments, the controller 52 may determine one or more physical characteristics of the patient, other than a temperature of the patient, based on the comparison. For example, if the controller 52 determines that the temperature of the forehead is within an acceptable range, such as between approximately 96 degrees Fahrenheit and approximately 98 degrees Fahrenheit, but that the temperature of the sinus region is above such an acceptable range, the controller 52 may conclude and/or otherwise determine that there is an injury and/or disease state associated with the sinus region. As used herein, the term "disease state" may be defined as any known infection, rash, disease, illness, ailment, condition, or other like medical abnormality associated with a patient. It is understood that such a physical characteristic determination may be dependent upon, for example, the various anatomical structures being observed and/or sensed by the sensing elements 48, and that such physical characteristics may further include happiness, sadness, nervousness, tension, laughter, fear, stress, excitement, and/or other emotional states.

Figure 9:
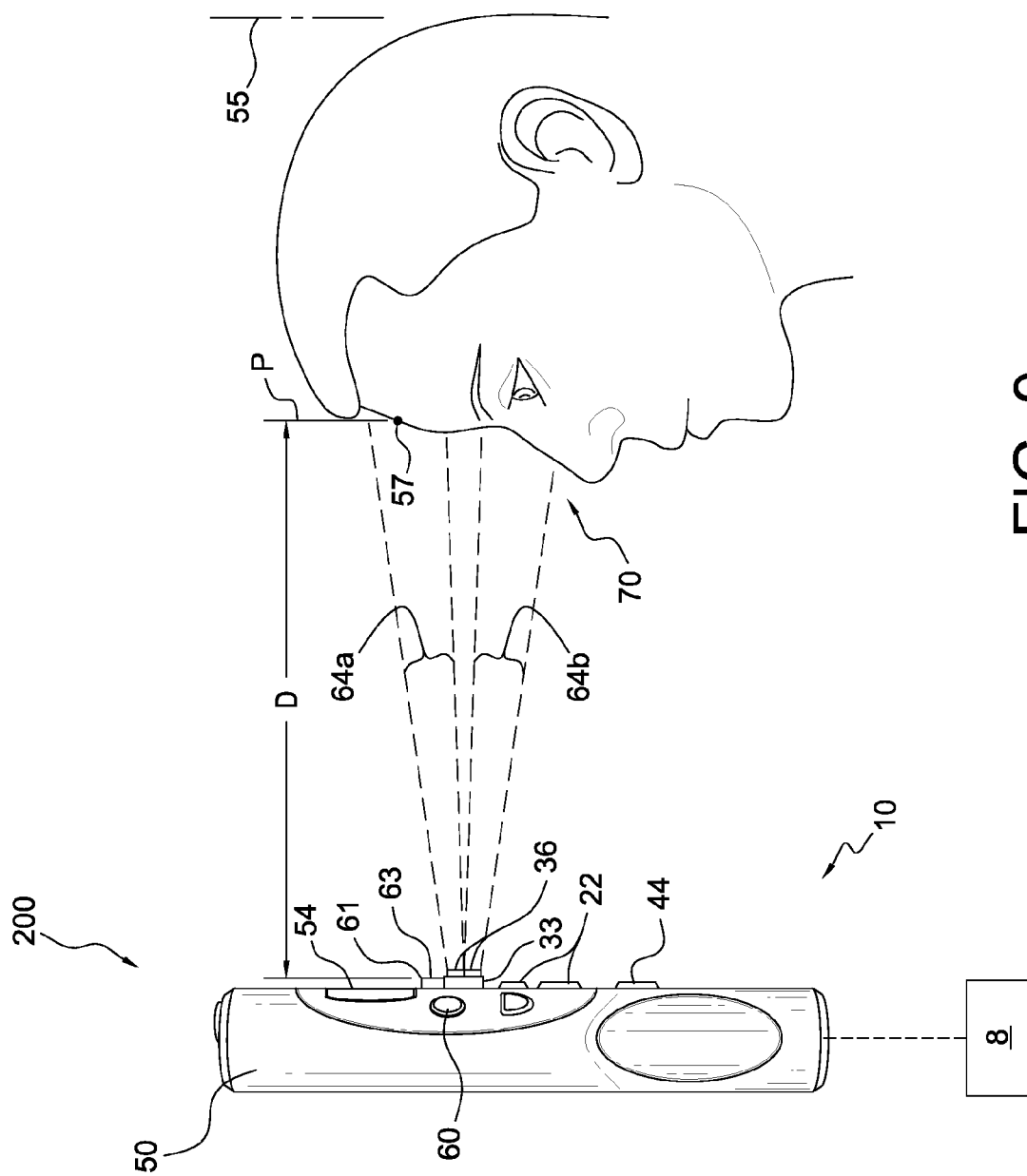
FIG. 9 is another exemplary view of the temperature measurement system shown in FIG. 8.

In still further exemplary embodiments, the temperature device 10 may include one or more sensors configured to determine a position of the temperature device 10 relative to another structure such as the patient. In exemplary embodiments, such a sensor may comprise a proximity sensor 61 configured to determine one or more alignment parameters associated with a position of the temperature device 10 relative to the patient. As shown in FIG. 4, such an alignment parameter may include a distance D between the temperature device 10 and the patient. Alternatively, as shown in FIG. 9, such an alignment parameter may include a distance D between the handpiece 50 and the patient. In exemplary embodiments, the distance D may be representative of a distance between a sensing surface 63 and/or other portion of the proximity sensor 61 and a plane P substantially defined by an outer surface 70 of the patient. As shown in FIGS. 4 and 9, the plane P may be substantially defined by a forehead of the patient and/or other like locations on the outer surface 70. The axis 57 may extend along the plane P, and in exemplary embodiments, the plane P may comprise and/or be substantially parallel to a coronal plane of the patient.

In exemplary embodiments, the sensor 33 may be characterized by a preferred proximity range. In such embodiments, the "preferred proximity range" may be defined as a distance range, wherein when the sensor 33 is employed to determine a temperature of an object, positioning the sensor 33 such that the object is within the preferred proximity range results in an accurate temperature determination by the sensor 33. Such a temperature determination may be considered "accurate" when the temperature measured using the sensor 33 without contacting the patient is within approximately 10 percent of the temperature measured using the sensor 32 via patient contact. In exemplary embodiments, the preferred proximity range may be between approximately 1 foot and approximately 6 feet. In further exemplary embodiments, such a preferred proximity range may be between approximately 1 foot and approximately 2 feet. In exemplary embodiments, the preferred proximity range of the sensor 33 may be defined by and/or may be a function of the sensitivity of the sensor 33, and/or a focal length of one or more of the optical components 36 associated with the sensor 33. As shown in FIGS. 4 and 9, one or more such optical components 36 may assist in forming, shaping, and/or otherwise configuring the field of view 64a, 64b associated with sensing elements 48 of the sensor 33. In such exemplary embodiments, the preferred proximity range of the sensor 33 may be substantially equal to the focal length of one or more such optical components 36. In exemplary embodiments, the preferred proximity range of the sensor 33 may comprise an additional alignment parameter associated with the temperature device 10.

In exemplary embodiments, the proximity sensor 61 may comprise one or more gyroscopes, accelerometers, and/or other components configured to determine an angular position of the temperature device 10 relative to another structure. For example, the proximity sensor 61 may be configured to determine the magnitude of one or more angles formed between the temperature device 10 and the plane P defined by the outer surface 70 of the patient. In exemplary embodiments, such an angle may be formed between the sensing surface 63 and/or any other portion of the proximity sensor 61 and the plane P. With respect to the embodiment shown in FIG. 4, such angles may be formed by, for example, rotating and/or otherwise moving the temperature device 10 about one or both of the axes 55, 57. Alternatively, with respect to the embodiment shown in FIG. 9, such angles may be formed by, for example, rotating and/or otherwise moving the handpiece 50 about one or both of the axes 55, 57. Such exemplary angles are illustrated in FIGS. 5 and 6.

For example, as shown in FIG. 5, rotating the sensor 61 and/or the temperature device 10 about the axis 55 may result in an angle $\Theta$ formed between the plane P and a normal line extending substantially perpendicularly from the sensing surface 63 of the sensor 61 through the axis 55. When the sensing surface 63 and/or the temperature device 10 is disposed substantially parallel to the plane P, an angle $\Theta_a$ equal to approximately 90 degrees may be formed between the plane P and the normal line. Alternatively, rotating the proximity sensor 61 and/or the temperature device 10 about the axis 55, such as by rotating the temperature device 10 about the face of the patient, may increase (angle $\Theta_c$) or decrease (angle $\Theta_b$) the magnitude of the angle $\Theta$ formed between the normal line and the plane P. In exemplary embodiments, the sensor 33 may determine a temperature of the outer surface 70 when the temperature device 10 is disposed substantially parallel to the outer surface 70 (i.e., when the angle $\Theta_a$ formed between the plane P and the normal line is equal to approximately 90 degrees). It is understood, however, that temperature determinations made by the sensor 33 may also have an acceptable accuracy for some applications when the angle $\Theta$ is within a desired angle range. Such a desired angle range for the angle $\Theta$ may be between approximately 75 degrees and approximately 105 degrees. The accuracy of such temperature determinations may be considered "acceptable" when the temperature measured using the sensor 33 without contacting the patient is within approximately 10 percent of a corresponding temperature measured using the sensor 32 via patient contact.

As shown in FIG. 6, rotating the sensor 61 and/or the temperature device 10 about the axis 57 may result in an angle $\alpha$ formed between the plane P and the normal line extending substantially perpendicularly from the sensing surface 63 of the sensor 61 through the axis 57. When the sensing surface 63 and/or the temperature device 10 is disposed substantially parallel to the plane P, an angle $\alpha_a$ equal to approximately 90 degrees may be formed between the plane P and the normal line. Alternatively, rotating the proximity sensor 61 and/or the temperature device 10 about the axis 57, such as by rotating the temperature device 10 from the forehead to the chin of the patient, may increase (angle $\alpha_c$) or decrease (angle $\alpha_b$) the magnitude of the angle $\alpha$ formed between the normal line and the plane P. In additional exemplary embodiments, one or more of the angles $\Theta$, $\alpha$ described herein may comprise additional alignment parameters associated with the temperature device 10. In exemplary embodiments, the sensor 33 may determine a temperature of the outer surface 70 when the temperature device 10 is disposed substantially parallel to the outer surface 70 (i.e., when the angle $\alpha_a$ formed between the plane P and the normal line is equal to approximately 90 degrees). It is understood, however, that in some applications the temperature determinations made by the sensor 33 may also have an acceptable accuracy when the angle $\alpha$ is within a desired angle range. Such a desired angle range for the angle $\alpha$ may be between approximately 75 degrees and approximately 105 degrees. As described above, the accuracy of such temperature determinations may be considered "acceptable" when the temperature measured using the sensor 33 without contacting the patient is within approximately 10 percent of a corresponding temperature measured using the sensor 32 via patient contact.

In further exemplary embodiments, the temperature device 10 may include one or more actuation devices (not shown) associated with the sensor 33. Such actuation devices may be operably connected to the controller 52 and may be configured to move the sensor 33 relative to the temperature device 10. For example, in the embodiment shown in FIG. 1 such actuation devices may be configured to pivot the sensor 33 relative to the handle 20 and/or any other portion of the temperature device 10. In such an exemplary embodiment, the one or more actuation devices may be configured to pivot the sensor 33 about a longitudinal axis (not shown) of the handle 20 and/or the temperature device 10. In further exemplary embodiments, such actuation devices may be configured to move the sensor longitudinally along the handle 20 and/or other portions of the temperature device. In exemplary embodiments, such movement may be substantially parallel to, for example, the longitudinal axis of the handle 20. In still further exemplary embodiments, such actuation devices may be configured to pivot the sensor 33 about an axis (not shown) extending substantially perpendicular to the handle 20 and/or other portions of the temperature device 10. In exemplary embodiments, such an axis may extend substantially perpendicular to the longitudinal axis of the handle 20. In still further exemplary embodiments, such actuation devices may be configured to move one or more of the optical components 36 relative to the temperature device 10. In such exemplary embodiments, the actuation devices may move the optical devices 36 in concert with or independently from movement of the sensor 33.

Alternatively, in the embodiment of FIG. 8 such actuation devices (not shown) may be configured to move the sensor 33 relative to the handpiece 50. Such movement may be analogous to the movement described above with respect to the sensor 33 and/or optical components 36 shown in FIG. 1. For example, in the embodiment of FIG. 8, such actuation devices may be configured to pivot the sensor 33 relative to the handpiece 50 and/or to move the sensor 33 along one or more surfaces of the handpiece 50. Such movement may be, for example, about, along, and/or substantially parallel to one or more axes of the handpiece 50. Additionally, in such exemplary embodiments the actuation devices may move one or more optical devices 36 in concert with or independently from movement of the sensor 33.

The exemplary actuation devices described above may comprise any electric motor, servo motor, and/or other known device configured to assist in moving one or more components of the sensor 33 relative to the temperature device. Accordingly, it may be possible to form any of the angles $\Theta$, $\alpha$ described herein with respect to FIGS. 5 and 6 through activation of one or more such actuation devices while maintaining the position of the temperature device 10 substantially stationary with respect to the plane P and/or the patient.

In exemplary embodiments the temperature device 10 may further include one or more signal devices 44 operably connected to the controller 52, the sensors 32, 33, and/or the proximity sensor 61. Such signal devices 44 may include, for example, one or more lights, LEDs, speakers, and/or other like devices configured to emit an audible and/or optical alarm or signal in response to a command or signal from the controller 52. Such an alarm or other signal may be initiated by, for example, the controller 52 when a temperature determined by the temperature device 10 meets or exceeds a threshold temperature. In additional exemplary embodiments, such an alarm or signal may be initiated during a substantially continuous temperature calculation operation where the rate of patient temperature change meets or exceeds a predetermined temperature change rate threshold. In further exemplary embodiments, such an alarm or signal may be initiated and/or otherwise communicated to a user of the temperature device 10 based on one or more of the alignment parameters described herein. For example, the signal device 44 may be configured to output information indicative of one or more such alignment parameters to assist the user in positioning the temperature device 10 and/or the sensor 33 relative to the patient. In exemplary embodiments, the signal device 44 may output an alarm or other signal indicating that the temperature device 10 and/or the sensor 33 is disposed outside of the preferred proximity range of the sensor 33. The signal device 44 may also be configured to output a signal indicating when the temperature device 10 and/or the sensor 33 has been positioned within the preferred proximity range. In a similar manner, the signal device 44 may be configured to output one or more signals or alarms indicative of one or more of the desired angle ranges described above with respect to the angles Θ, α.

As discussed above, and as illustrated in FIGS. 1, 3, 4, 7, 8, and 9, the temperature device 10 may include one or more displays 54. An exemplary display 54 may be operably connected to the controller 52 and/or to the image processor 53. The display 54 may comprise, for example, a liquid crystal display (LCD) screen, a light emitting diode (LED) display, a digital read-out, an interactive touch-screen, and/or any other like components configured to communicate information to the user or control the temperature device 10. Such displays 54 may be configured to indicate, for example, one or more temperatures determined by the sensors 32, 33, one or more temperatures determined based on signals received from the sensors 32, 33, and/or any other information that may be useful during operation of the temperature device 10. For example, the display 54 may also be configured to communicate information indicative of the alignment parameters described herein. The display 54 may also be configured to communicate information indicative of additional physical characteristics of the patient including but not limited to disease state, injury, and emotional state. The display 54 may be configured to communicate such information substantially instantaneously and/or substantially continuously depending on the mode of operation of the temperature device 10. Such a display 54 may also indicate whether or not the temperature device 10 is turned on, and whether a probe cover 30 has been connected to the temperature device 10. Although in the exemplary embodiment of FIG. 8 the sensor 33, signal device 44, operator interfaces 22, imaging device 60, and sensor 61 are shown as being disposed on the same side of the handpiece 50 as the display 54 (i.e., a "front" side of the handpiece 50), in additional exemplary embodiments, one or more of these components may be disposed on, for example, a different side of the handpiece 50 than the display. For example, one or more such components may be disposed on a "rear" side of the handpiece 50 opposite the front side shown in FIG. 8.

In each of the exemplary embodiments described herein, one or more of the signal device 44 and the display 54 may be configured to request and/or direct movement of the patient relative to the temperature device 10. In such embodiments, for example, the signal device 44 and/or the display 54 may output one or more audible and/or visual signals or requests informing the user where to position the patient. Such requests may comprise, for example, one or more visual alignment beams, visual images, and/or audible communications/instructions indicating a desired patient movement relative to a substantially stationary temperature device 10. In still further embodiments, such requests may comprise visual instructions including one or more indicator lights on the temperature device 10. Such indicator lights may, for example, be illuminated sequentially as the patient moves closer to or further from a desired location relative to the temperature device 10. The requests and/or instructions described herein may assist the sensor 33, imaging device 60, and/or other components of the temperature device 10 to sense, measure, observe, read, and/or otherwise survey the outer surface 70 in a systemic manner while the temperature device 10 is maintained substantially stationary. In exemplary embodiments, the instructions and/or requests may be based on one or more of the alignment parameters and/or preferred proximity ranges described herein. In addition, in such embodiments the actuation devices described herein may be omitted. Accordingly, such instructions and/or requests may assist in forming the two or three-dimensional image, temperature gradient, and/or temperature profile of the patient as described above.

Additionally, in exemplary embodiments in which the imaging device 60 described above comprises a digital camera operably connected to the controller 52 and configured to capture an image of the outer surface 70 and/or other portions of the patient, the imaging device 60 may be substantially aligned with and/or otherwise spatially associated with the sensor 33. In such embodiments, the imaging device 60 may be utilized to capture one or more digital images of the patient, and the images may be utilized by a user of the temperature device 10 to assist in positioning the temperature device 10 prior to and/or while sensor 33 determines one or more physical characteristics of the patient. For example, the images captured by the imaging device 60 may be shown on the display 54 while the sensor 33 is operable to assist in aligning the temperature device 10. In such embodiments, such images may comprise still photos or real-time video images. Such images may include, for example, a visual illustration of the outer surface 70 of the patient, as well as a visual illustration of one or more of the alignment parameters and/or preferred proximity ranges described herein superimposed onto the illustration of the outer surface 70. Such images may assist the user in positioning the temperature device 10 prior to and/or during use.

In additional exemplary embodiments, the temperature device 10 may include one or more transmitters, receivers, transceivers and/or other like communication devices (not shown) configured to send information to and/or receive information from a remote device and/or source. In such exemplary embodiments, the temperature device 10 may be configured to send and/or receive any of the information described herein with regard to the display 54, sensors 32, 33, and/or other components of the temperature device 10 via such communication devices. In such embodiments, a communication device of the temperature device 10 may be configured to send and/or receive such information to a remote device and/or source wirelessly via BLUETOOTH®, WIFI®, or other like means. Such a communication device may be disposed at any convenient location on the temperature device 10, and in additional embodiments, such a communication device may be disposed partially and/or completely internal to the temperature device 10.

The display 54 may also be configured to indicate one or more modes of operation of the temperature device 10. Such modes of operation may include, for example, substantially continuous or instantaneous modes of temperature determination. Such modes of operation may also include a first operating mode where the temperature device 10 is configured to measure a first temperature of the patient without contacting the patient with the temperature device 10 (i.e., a noncontact-based temperature), and to determine a first temperature value indicative of a core temperature of the patient based on the first temperature. Such modes of operation may also include a second operating mode in which the temperature device 10 is configured to measure a second temperature of the patient by contacting a measurement site of the patient with at least a portion of the temperature device 10 (i.e., a contact-based temperature), and to determine a second temperature value indicative of the core temperature of the patient based on the second temperature. Such modes of operation may also include a third operating mode in which the temperature device 10 is configured to measure the first and second temperatures described above, and to determine a third temperature value indicative of the core temperature of the patient based on the first and second temperatures. In the exemplary embodiments described above, when the temperature device 10 is operating in the first operating mode, the first temperature value may be determined without regard to the second temperature. Moreover, when the temperature device 10 is operating in the second operating mode, the second temperature value may be determined without regard to the first temperature. As will be described in greater detail below, while operating in such exemplary first and third operating modes, the controller 52 of the temperature device 10 may also utilize inputs from one or more of the additional sensors described herein. Such inputs may facilitate determining physical characteristics of the patient in addition to, for example, temperature values indicative of core temperature.

In still further exemplary embodiments, the display 54 may be configured to communicate information indicative of whether one or more threshold temperatures, threshold temperature change rates, and/or other sensed metric thresholds have been met or exceeded. The display 54 may be configured to display any other typical operating information such as, for example, a temperature vs. time trend line or other graphical depictions.

As described above with respect to FIG. 3, the display 54 may be configured to illustrate a visual image 72 of the patient. Additionally, as described above with respect to FIG. 7, the display 54 may be configured to illustrate a two-dimensional or three-dimensional thermal image 74 indicative of patient temperature. Such two or three-dimensional thermal images 74 may comprise, for example, two or three-dimensional temperature profiles corresponding to an outer surface 70 of the patient. Such temperature profiles may be formed using temperature measurements obtained with, for example, one or more of the sensing elements 48 associated with the sensor 33 described above. Such temperature profiles may assist in determining, for example, a disease state, injury, emotional state, and/or other physical characteristics of the patient. For example, as shown in the thermal image 74 of FIG. 7, such temperature profiles may illustrate areas of relatively high temperature (referred to herein as "hot spots" 77) associated with the outer surface 70. Such hot spots 77 may be indicative of a relative difference in blood pressure, temperature, and/or other like characteristics at the imaged location on the outer surface 70. Such relative differences may be useful in identifying, for example, an injury or a disease state associated with the location. Such hot spots 77 may also be indicative of happiness, sadness, nervousness, tension, laughter, fear, stress, excitement, and/or other physical characteristics or emotional states.

In exemplary embodiments, the display 54, the controller 52, the image processor 53, the sensor 33, the imaging device 60, and/or other components described herein may assist in correlating such hot spots 77 to, for example, a visual image 72 of the patient. In such exemplary embodiments, the visual image 72 may be stored in a memory of the controller 52 and/or may be obtained using the imaging device 60. In exemplary embodiments, the display 54 may assist in such correlation by, for example, superimposing the three-dimensional thermal image 74 over the visual image 72 such that both images 72, 74 are displayed at the same time and/or are otherwise correlated. It is understood that such correlation may also be performed by the controller 52 without displaying one or both of the images 72, 74.

The controller 52 may be operably connected to the operator interfaces 22, display 54, sensors 32, 33, imaging device 60, proximity sensor 61, and/or other components of the temperature device 10, and the controller 52 may be configured to control the operation of such components. In an exemplary embodiment, the controller 52 may be configured to receive signals, information, measurements, and/or other data from the sensors 32, 33 of the temperature device 10, and to determine a temperature value indicative of a core temperature of the patient based on the information received. The controller 52 may also be configured to execute one or more commands and/or control programs. In addition to the image processor 53 described above, the controller 52 may comprise memory, additional processors, and/or other known controller components to facilitate the functionality described herein. In an exemplary embodiment, the controller 52 may be disposed within, for example, the handle 20 of the temperature device 10. In such an embodiment, the handle 20 may form one or more substantially water-tight and/or substantially hermetically sealed compartments for storing the various components of the controller 52. Alternatively, as shown in FIG. 8, the controller 52, image processor 53, memory, additional processors, and/or other known controller components may be disposed within the handpiece 50. In such an embodiment, the handpiece 50 may form one or more substantially water-tight and/or substantially hermetically sealed compartments for storing such controller components.

Figure 2:
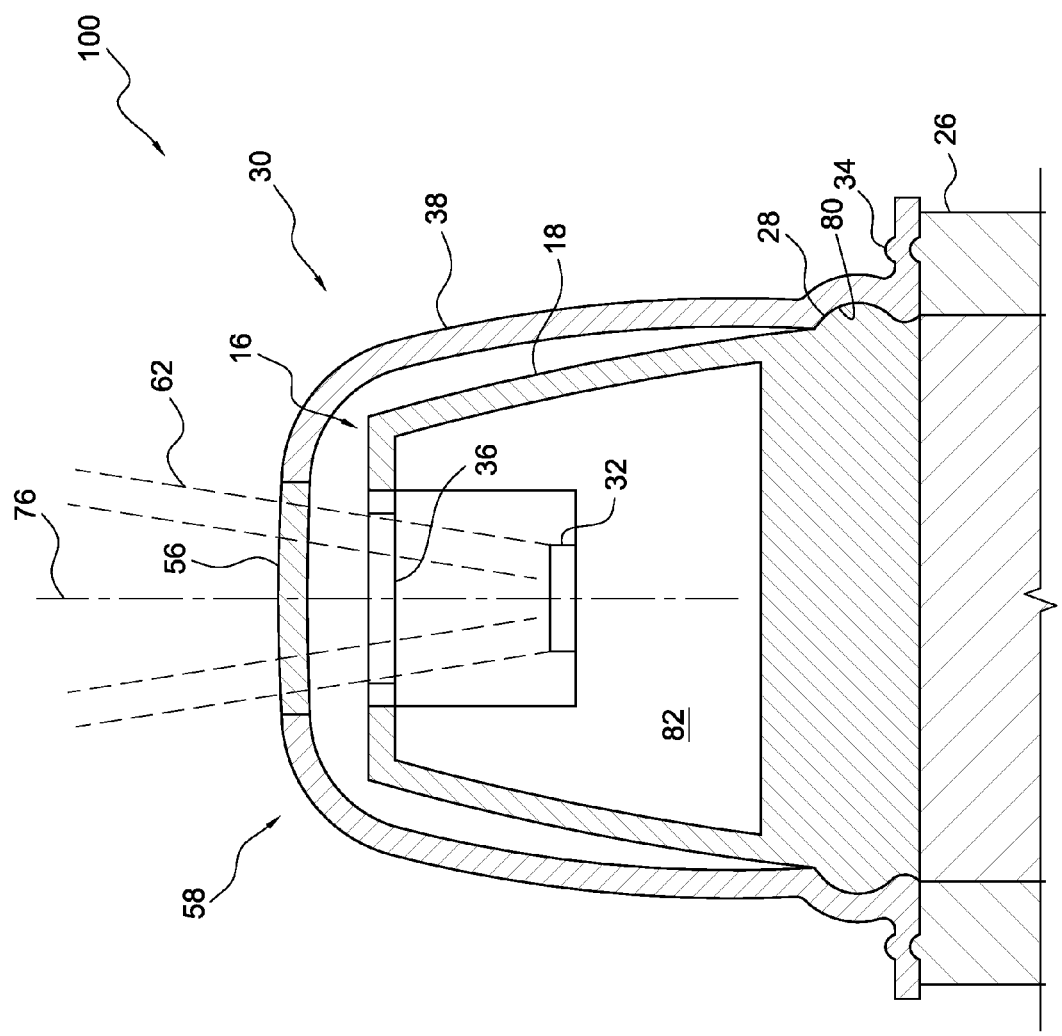
FIG. 2 illustrates a cross-sectional view of a portion of the temperature measurement system shown in FIG. 1.

In exemplary embodiments, the probe cover 30 may include a body 38 having a distal end 40, a proximal end 42, and a substantially atraumatic tip 58 disposed at the distal end 40. As shown in FIGS. 1 and 2, in exemplary embodiments the probe cover 30 may also include an annular flange 34 disposed at the proximal end 42. The body 38 may be substantially conical, substantially cylindrical, and/or any other suitable shape, and in exemplary embodiments, the body 38 may be similar in shape, size, and/or dimensions to the head 18. For example, the probe cover 30 may be hollow, and the body 38 may be incrementally longer than the head 18 so as to fit over substantially the entire head 18. When mounted on the temperature device 10 shown in FIG. 1, the probe cover 30 may overlay the sensor 32 disposed at the tip 16 of the head 18. The probe cover 30 may define an orifice 46 at the proximal end 42 thereof. The probe cover 30 may have a longitudinal axis 76 extending centrally through the body 38 and the tip 58, and when the probe cover 30 is connected to the temperature device 10 shown in FIGS. 1 and 2, the longitudinal axis 76 may be substantially collinear with, for example, a central and/or longitudinal axis (not shown) of the sensor 32.

Alternatively, with respect to the embodiment shown in FIG. 8 the probe cover 30 may have similar dimensions to that of the shaft 19. For example, the probe cover 30 shown in FIG. 8 may be incrementally longer than the shaft 19 so as to fit over substantially the entire shaft 19.

The probe covers 30 described herein may be formed from any medically approved material known in the art. Such materials may include, for example, plastics, polymers, and/or any of the other materials discussed above with regard to the temperature device 10. Using such materials may enable, for example, the probe cover 30 to be repeatedly used and/or sanitized. Such materials may also facilitate formation of the probe cover 30 through any molding, extrusion, and/or other like process known in the art. Such materials and/or processes may enable the probe cover 30 to be formed with any desirable transmissivity, thickness, dimensions, and/or other configurations.

In exemplary embodiments, the probe cover 30 may include one or more optical components 56 disposed proximate the distal end 40. In an exemplary embodiment, at least one of the optical components 56 may be disposed flush with and/or form at least a portion of the tip 58. Alternatively, at least one of the optical components 56 may be disposed flush with and/or form at least a portion of the body 38 proximal to the tip 58. The optical components 56 may be similar to the optical components 36 described above with respect to the head 18. For example, the optical components 56 may comprise one or more windows, mirrors, lenses, filters, or other like components, and in an exemplary embodiment, the optical components 56 may comprise one or more divergent, collimating, and/or convergent lenses. Such optical components 56 may assist in focusing, guiding, and/or otherwise directing radiation 62 to the sensor 32.

The probe cover 30 may also include one or more structures to facilitate usage with, connection to, and/or removal from the temperature device 10. For example, while the orifice 46 of the probe cover 30 illustrated in FIGS. 1 and 2 may be shaped, sized, and/or otherwise configured to accept the head 18 and to mate with one or more ejector mechanisms 26 of the temperature device 10, in further exemplary embodiments, at least a portion of the proximal end 42 of the probe cover 30 may include additional notches, cutouts, tabs, ribs, flanges, and/or other retention components 80 configured to assist in connecting the probe cover 30 to and/or disconnecting the probe cover 30 from the temperature device 10. The retention components 80 of the probe cover 30 may be shaped, sized, located, and/or otherwise configured to mate with the retention components 28 of the head 18. Once the probe cover 30 has been connected to the temperature device 10, the retention components 80 of the probe cover 30 may assist in providing a retention force sufficient to maintain the connection between the probe cover 30 and the temperature device 10. An exemplary retention force may be a compression force applied by, for example, a semi-circular and/or otherwise concave retention component 80 of the probe cover 30 to one or more convex retention components 28 proximate the base 24 of the head 18.

As shown in FIGS. 1 and 2, the flange 43 may form part of the one or more retention components 80. Alternatively, the flange 34 may be disposed proximate the one or more retention components 80 such as, for example, proximal to the retention components 80. At least a portion of the flange 34 may extend substantially perpendicular to the longitudinal axis 76, and an exemplary embodiment of the flange 34 may include one or more camming surfaces positioned such that the ejector mechanism 26 is able to ride along the one or more camming surfaces to assist in bending and/or otherwise flexing a portion of the probe cover 30. The force applied by the ejector mechanism 26 to the one or more camming surfaces of the probe cover 30 may be sufficient to overcome the retention force provided by the retention components 80, and as a result, the probe cover 30 may be ejected from the head 18.

Alternatively, the orifice 46 of the probe cover shown in FIG. 8 may be shaped, sized, and/or otherwise configured to accept the shaft 19 and to mate with one or more stationary retention components 27 of the temperature device 10. In further exemplary embodiments, at least a portion of the proximal end 42 of the probe cover 30 shown in FIG. 8 may include additional notches, cutouts, tabs, ribs, rings, flanges, and/or other retention components (not shown) configured to assist in connecting the probe cover 30 to and/or disconnecting the probe cover 30 from the temperature device 10. For example, such retention components of the probe cover 30 may mate with the stationary retention components 27 of the temperature device 10 to facilitate retention of the probe cover 30 on the shaft 19 and/or ejection of the probe cover 30 from the shaft 19.

The exemplary temperature measurement systems 100, 200 described herein may be utilized by physicians, nurses, health care professionals, and/or other users in a variety of different environments. For example, the temperature devices 10 and/or temperature measurement systems 100, 200 described herein may be employed in any of a number of examination facilities to determine one or more temperatures associated with a patient such as, for example, an estimated core temperature of the patient. Such an estimated core temperature may be utilized by the health care professional to assist in treating the patient, and may have a variety of uses that are well known in the medical field.

The exemplary temperature measurement systems 100, 200 may be utilized to determine patient temperature in a variety of different ways. For example, the temperature devices 10 disclosed herein may be configured to determine patient temperature using one or more contact-based methods of temperature determination. In such contact-based methods, a "contact" mode of the temperature device 10 may be selected using one or more of the operator interfaces 22 described herein. Additionally, a user of the temperature device 10 may insert at least a portion of the temperature device 10 into a corresponding probe cover 30. The user may insert at least a portion of, for example, the head 18 into the probe cover 30, via the orifice 46. Alternatively, in the embodiment shown in FIG. 8, the user may insert at least a portion of the shaft 19 into the prove cover 30 via the orifice 46. In an exemplary embodiment, the probe cover 30 may be disposed within a box or other like storage container (not shown) while the head 18 (or the shaft 19) of the temperature device 10 is inserted into the probe cover 30. In such an exemplary embodiment, the probe cover 30 may be accessed through an opening of the storage container for insertion of the head 18 or shaft 19.

As one or more of the retention components 27, 28 of the temperature device 10 comes into contact with the probe cover 30, the retention components 27, 28 may hook, clip, and/or otherwise mate with the proximal end 42 of the probe cover 30 to assist in retaining the probe cover 30. In exemplary embodiments in which the proximal end 42 of the probe cover 30 defines one or more of the notches, cutouts, and/or other concave retention components described above, these retention components may mate with the corresponding retention components 27, 28 of the temperature device 10 to assist in retaining the probe cover 30 thereon.

Once the probe cover 30 has been mounted onto the temperature device 10, the probe cover 30 may be placed into contact with a patient measurement site to facilitate determining an estimated core temperature of the patient. For example, at least a portion of the probe cover 30 shown in FIG. 1 may be inserted into an ear canal of the patient such that the tip 58 is disposed proximate the tympanic membrane of the patient. The probe cover 30 and/or the sensor 32 may be positioned such that the probe cover 30 is in contact with the ear and/or ear canal, and the tympanic membrane is disposed at least partially within the field of view of the sensor 32. Alternatively, in the exemplary embodiment shown in FIG. 8, the probe cover 30 may be inserted into an axilla area, a rectal cavity, an oral cavity, and/or other like patient measurement site such that the tip 58 is disposed in contact with the measurement site.

Once the probe cover 30 has been placed in contact with the patient measurement site, the sensor 32 may be activated via the operator interfaces 22 to sense a temperature indicative of a temperature of the patient measurement site. For example, in an embodiment in which the sensor 32 comprises a thermocouple and/or a thermistor, the sensor 32 may be utilized to measure the temperature of the measurement site. Alternatively, in embodiments in which the sensor 32 comprises an infrared temperature sensor, the sensor 32 may detect radiation 62 emitted by the measurement site. For example, radiation 62 emitted by the tympanic membrane, oral cavity, axilla area, and/or rectal cavity may be directed to the sensor 32 for collection via the one or more optical components 56. Signals indicative of the patient measurement site temperature may be sent to the controller 52 by the sensor 32, and while the temperature device is operating in the contact mode, the controller 52 may assist in estimating the core temperature based solely on this sensed temperature.

In additional exemplary embodiments, the temperature devices 10 disclosed herein may be configured to determine patient temperature and/or other physical characteristics of the patient using one or more noncontact-based methods of patient evaluation. In such noncontact-based methods, a "noncontact" mode of the temperature device 10 may be selected using one or more of the operator interfaces 22 described herein. In such exemplary noncontact modes of operation, the sensor 33 may be activated via the operator interfaces 22 to determine a temperature indicative of a temperature of the patient measurement site. For example, in an embodiment in which the sensor 33 comprises a thermocouple, a thermopile, and/or an infrared temperature sensor, the sensor 33 may detect radiation 62 emitted by the measurement site. For example, radiation 62 emitted by the forehead, eyes, sinus area, and/or other locations on the outer surface 70 of the patient may be collected by the sensor 33. Such radiation may be directed to the sensor 33 for collection via the one or more optical components 36 associated with the sensor 33. Signals indicative of the patient measurement site temperature may be sent to the controller 52 by the sensor 33, and while the temperature device 10 is operating in the noncontact mode, the controller 52 may assist in estimating the core temperature based solely on this sensed noncontact-based temperature. Such noncontact-based methods of temperature determination may be useful in a variety of applications. Such applications may include initial and/or patient intake screening, and situations in which the patient is uncooperative. Such applications may also include situations in which temperature determination through traditional contact-based methods may place the user at an elevated risk of contact with, for example, germs, viruses, contagious disease, patient bodily fluids, and/or other like substances or contaminants.

Figure 10:
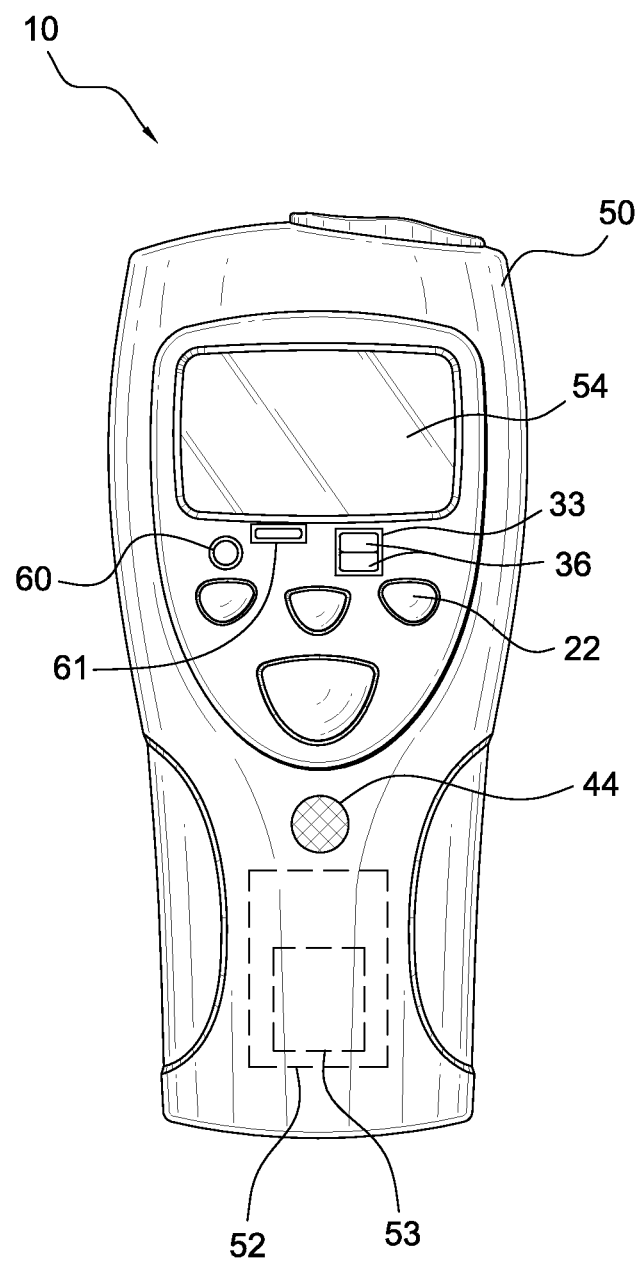
FIG. 10 illustrates a temperature measurement system according to a further exemplary embodiment of the present disclosure.

In exemplary embodiments in which the temperature device 10 is configured to determine patient temperature and/or other physical characteristics using a noncontact-based method of patient evaluation, one or more components of the temperature device 10 associated with contact-based methods of patient evaluation may be omitted. For example, in such embodiments the sensor 32 and corresponding optical components 36 may be omitted from the temperature device 10. Additionally, with regard to the exemplary temperature device 10 shown in FIG. 8, the shaft 19, handle 20, and/or the entire probe 8 may be omitted. Omission of such components may reduce the cost and complexity of the temperature device 10 and may be desirable in environments in which noncontact-based patient evaluation methods are adequate for the level of care required. Such an exemplary device is illustrated in FIG. 10.

In further exemplary embodiments, the temperature devices 10 disclosed herein may be configured to determine one or more physical characteristics of a patient, including but not limited to patient temperature, using a combination of a contact-based method of temperature determination and a noncontact-based method of temperature determination and/or patient evaluation. In such methods, a "combination" mode of the temperature device 10 may be selected using one or more of the operator interfaces 22 described herein. Such a combination mode may be useful to assist in determining a variety of physical characteristics of the patient based on one or more comparisons between contact-based and noncontact-based method of patient evaluation. Further, it is understood that the temperature devices 10 of the present disclosure may allow the user to select between the contact mode, noncontact mode, and combination mode of operation depending upon the requirements of each particular application and/or the condition or characteristics of the patient.

While operating in the combination mode, an exemplary method of temperature determination may include determining one or more alignment parameters associated with the position of the temperature device 10 relative to the patient. Such an alignment parameter may be determined using one or more of the sensors described herein, and the alignment parameter may be determined before, during, and/or shortly after determining the temperature indicative of the temperature of the measurement site with the sensor 33. In such embodiments, a temperature value indicative of the patient's core temperature may be determined based on the alignment parameter.

For example, as described above with respect to the embodiments of FIGS. 4, 5, 6, and 9, the alignment parameter may include a distance D between the temperature device 10 and the patient. In such embodiments, the distance D may be a distance between the sensing surface 63 of the proximity sensor 61 and the plane P substantially defined by the outer surface 70 of the patient. In such embodiments, the plane P may be substantially defined by, for example, the forehead of the patient and/or other like locations on the outer surface 70. Such locations on the outer surface 70 may define and/or otherwise include the patient measurement site. In such exemplary embodiments, the distance D may be determined when the sensing surface 63 is disposed substantially parallel to the plane P.

Additionally, the alignment parameter may comprise an angle $\Theta$, $\alpha$ formed between the temperature device 10 and the plane P. For example, such angles $\Theta$, $\alpha$ may be formed between the sensing surface 63 of the proximity sensor 61 and the plane P. In the exemplary embodiments shown in FIGS. 5 and 6, such angles $\Theta$, $\alpha$ may be formed between the plane P and a normal line extending substantially perpendicularly from the sensing surface 63. As shown in FIG. 5, various angles $\Theta$ may be formed between the normal line and the plane P when the normal line passes through the axis 55. Moreover, as shown in FIG. 6, various angles $\alpha$ may be formed between the normal line and the plane P when the normal line passes through the axis 57.

In exemplary embodiments, the temperature value indicative of the core temperature of the patient may be determined based on one or more of the alignment parameters described herein. For example, noncontact-based temperature determinations made by the sensor 33 may be most accurate when, for example, the sensor 33 is disposed within the preferred proximity range described above. If the measured distance D is within the preferred proximity range of the sensor 33, the controller 52 may increase, decrease, and/or otherwise modify, for example, a temperature value measured by the sensor 33 based on the distance D. For example, a distance $D_P$ associated with a peak accuracy of the sensor 33 may be stored within a memory of the controller 52, and the controller 52 may decrease a temperature value measured by the sensor 33 as a function of a measured distance $D_1$ less than the distance $D_P$. Such a distance $D_1$ may indicate that the sensor 33 is disposed closer to the plane P than desired for peak accuracy. The controller 52 may also be configured to increase a temperature value measured by the sensor 33 as a function of a measured distance $D_2$ greater than the distance $D_P$. Such a distance $D_2$ may indicate that the sensor 33 is disposed further from the plane P than desired for peak accuracy. In such embodiments, the controller 52 may increase or decrease the temperature value measured by the sensor 33 based on one or more algorithms, look-up tables, maps, and/or other like means. In still further exemplary embodiments, if the measured distance D is outside of the preferred proximity range of the sensor 33, the controller 52 may provide a corresponding alarm, signal, and/or other like message to the user via the display 54 and/or the signal device 44. It is understood that the distances $D_P$, $D_1$, and $D_2$ described herein are merely exemplary, and these distance are not illustrated in FIGS. 1-9.

Likewise, the non-contact-based temperature determinations made by the sensor 33 may be most accurate when, for example, the angles Θ, α formed between the sensing surface 63 of the proximity sensor 61 and the plane P are within the respective acceptable angle ranges described above. If the measured angles Θ, α are within the respective acceptable angle ranges, the controller 52 may increase, decrease, and/or otherwise modify, for example, a temperature value measured by the sensor 33 using methods similar to those described above with respect to the distances $D_P$, $D_1$, and $D_2$. For example, angles Θa, αa substantially equal to 90 degrees may be associated with a peak accuracy of the sensor 33, and such respective angles Θa, αa may be stored within a memory of the controller 52. The controller 52 may increase or decrease a temperature value measured by the sensor 33 as a function of the difference between a measured angle $Θ_b$, $α_b$, and the corresponding angle Θa, αa stored in the memory of the controller 52. In still further exemplary embodiments, if one of the measured angles $Θ_b$, $α_b$ is outside of the respective acceptable angle range of the sensor 33, the controller 52 may provide a corresponding alarm, signal, and/or other like message to the user via the display 54 and/or the signal device 44.

While operating in the combination mode, another exemplary method of temperature determination may include generating a three-dimensional temperature profile of the patient. As illustrated in FIG. 7, such a three-dimensional temperature profile may be represented in a three-dimensional thermal image 74. Such an image 74 may be shown on the display 54. In such exemplary embodiments, the sensor 33 may measure temperature from a plurality of different locations on the outer surface 70 of the patient without contacting the patient. For example, the sensor 33 may determine a plurality of temperatures associated with different locations on the outer surface 70, and the user may move the temperature device 10 relative to the patient to facilitate measurement of such different locations. As described above, moving the temperature device 10 relative to the patient may include, for example, rotating the temperature device 10 about one or more axes 55, 57 substantially defined by the patient. Such movement may also include movement relative to the plane P described above. Alternatively, the temperature device 10 may remain substantially stationary relative to the patient, and the sensor 33 may be moved relative to the temperature device 10 using one or more actuation devices associated with the sensor 33.

In still further exemplary embodiments, sensing temperature from a plurality of different locations on the outer surface 70 of the patient without contacting such locations may include focusing sensing elements 48 of a sensor array of the temperature device 10 on different respective locations. As illustrated in FIG. 3, such an array of sensing elements 48 may be included in the sensor 33, and such sensing elements 48 may be substantially simultaneously focused on the respective different locations. For example, the first plurality 66 of sensing elements 48 may be focused on a first location of the outer surface 70 through the use of one or more of the optical components 36 described herein. In such exemplary embodiments, the second plurality 68 of sensing elements 48 may be focused on a second location of the outer surface 70 through the use of one or more additional optical components 36.

By focusing, for example, one or more sensing elements 48 of the sensor 33 in this way, exemplary embodiments of the temperature device 10 may be configured to only use temperature measurements and/or other inputs corresponding to the locations on the outer surface 70 that are brought within the field of view 64a, 64b of the respective sensing elements 48. In such embodiments, computations utilized to determine patient temperature using such inputs may be simplified, and the accuracy of the resulting temperature determinations may be increased. Additionally, in such exemplary embodiments the array associated with the sensor 33 may be constructed with fewer sensing elements 48 (i.e., without a number of pixels that would ordinarily be associated with locations on the outer surface 70 that are not focused on by the optical components 36), thereby reducing the overall cost of the temperature device 10.

While operating in the combination mode, another exemplary method of temperature determination may include correlating sensing elements 48 of the sensor arrays described herein to one or more respective anatomical structures of the patient using an image of the patient. For example, the imaging device 60 of the temperature device 60 may be used to capture a visual image 72 of the patient including, for example, the outer surface 70 and/or other portions of the patient. The respective anatomical structures may be included in the image. In still further exemplary embodiments, the imaging device 60 and/or the sensor 33 may be employed to form a thermal image 74 of the outer surface 70. The image processor 53 of the controller 52 may then employ one or more algorithms, software routines, and/or feature recognition programs to identify various anatomical structures appearing in the image 72, 74. Once such anatomical structures have been identified, one or more sensing elements 48 of the sensor 33 may be associated with a respective anatomical structure. A temperature value indicative of the core temperature of the patient may then be determined based on such a correlation.

For example, by associating one or more sensing elements 48 of the sensor 33 with an identified anatomical structure based on an image 72, 74, exemplary embodiments of the temperature device 10 may be configured to only use temperature measurements and/or other inputs received from locations on the outer surface 70 having a known temperature correlation to temperature measurements taken orally, at the axilla area, at the ear canal, at the rectal cavity, and/or at other traditional temperature measurement locations. In such embodiments, computations utilized to determine patient temperature using such inputs may be simplified, and the accuracy of the resulting temperature determinations may be increased. Additionally, in such exemplary embodiments the array associated with the sensor 33 may be constructed with fewer sensing elements 48 (i.e., without a number of pixels associated with locations on the outer surface 70 that do not show a strong correlation to temperature measurements taken at traditional temperature measurement locations), thereby reducing the overall cost of the temperature device 10.

While operating in the combination mode, another exemplary method of temperature determination may include determining one or more physical characteristics of the patient other than temperature values indicative of the core temperature. For example, the temperature devices 10 described herein may be configured to correlate one or more sensing elements 48 with a first anatomical structure of the patient using one of the images 72, 74 described above, and may measure a first temperature associated with the first anatomical structure using the one or more sensing elements. The temperature devices 10 may also be configured to correlate one or more different sensing elements 48 with a second anatomical structure different than the first anatomical structure using the image 72, 74, and may measure a second temperature associated with the second anatomical structure using the one or more different sensing elements 48. The controller 52 may then determine, for example, a disease state, an injury, and/or an emotional state of the patient based on a comparison between the measured temperatures. Such comparison-based determinations of patient condition may further assist the user in treating and caring for the patient by providing more information to the user than typically provided by traditional temperature devices.

In another exemplary combination mode of operation, the user may measure a first temperature of the patient, using sensor 33, without contacting the patient with any portion of the temperature device 10. The user may also measure a second temperature of the patient, using sensor 32, by contacting a patient measurement site with the temperature device 10. The controller 52 may then determine a temperature value indicative of the core temperature of the patient based on the first and second temperatures. In such embodiments, the controller 52 may be configured to modify the second (contact-based) temperature determined with sensor 32 based on the first (noncontact-based) temperature determined with sensor 33. Alternatively, the controller 52 may be configured to modify the noncontact-based temperature determined with sensor 33 based on the contact-based temperature determined with sensor 32.

In exemplary embodiments, the controller 52 may assign an arithmetic bias and/or other like weight factor to one or both of the first and second temperatures. Such a weight factor may be indicative of, for example, a priority of one of the determined temperatures relative to the other determined temperature, and such a relative priority may be useful when determining the core temperature of the patient. Such a weight factor may comprise, for example, a constant and/or other like coefficient associated with the one or more determined temperatures, and such coefficients may be part of a core temperature determination algorithm employed by the controller 52. The controller 52 may determine and/or associate such a weight factor with one or more of the determined temperatures described herein by using one or more weight factor look-up tables and/or weight factor data maps stored in a memory of the controller 52. Moreover, the controller 52 may be configured to modify one of the determined temperatures based on the other determined temperature and the weight factor assigned and/or otherwise associated with at least one of the determined temperatures.

For example, if the contact-based temperature determined by the sensor 32 indicates a patient measurement site temperature that is within an acceptable range, such as a temperature that is within approximately 1 percent of 98 degrees Fahrenheit, but the noncontact-based temperature determined by sensor 33 indicates an outer surface temperature that is outside of such an acceptable range, the controller 52 may adjust and/or otherwise modify the contact-based temperature to more closely match the noncontact-based temperature. Such a modification may be based on the weight factor associated with one or both of the determined temperatures, and such weight factors may be indicative of the relative correlation between such temperatures and the actual core temperature of the patient. Moreover, such a modification may be performed by nature of the one or more algorithms employed to determine the core temperature of the patient.

In exemplary embodiments, the controller 52 may be configured to modify the weight factor associated with at least one of the determined temperatures. For example, the controller 52 may modify a weight factor associated with a determined temperature based on a temperature value determined by the controller 52 indicative of the core temperature of the patient. In such embodiments, the controller 52 may, for example, compare the initial weight factor associated with a determined temperature to one or more different weight factors previously utilized when determining a temperature value indicative of the core temperature of the respective patient. For example, the controller 52 may extrapolate between the current weight factor and the different weight factor previously used to determine a modified weight factor for future temperature determinations. In exemplary embodiments, the controller 52 may modify the weight factor associated with at least one of the first and second determined temperatures described above, and the temperature device 10 may then measure a third temperature of the patient using one of the sensors 32, 33. In such embodiments, the controller 52 may determine an additional temperature value representative of the core temperature of the patient based on the modified weight factor and the additional temperature. Such modifications to the weight factor and/or to the one or more determined temperatures may be performed on a closed-loop basis and may result in a more accurate core temperature determination.

In additional exemplary embodiments in which the combination mode of operation is employed, any of the additional sensors described herein may be utilized to provide information to the user relevant to the patient's health. For example, contact-based temperature determinations made using the sensor 32 may be combined by the controller 52 with information received from the imaging device 60, proximity sensor 61, and/or other like sensors of the temperature device 10 to assist the user in determining information indicative of one or more of the physical characteristics described herein. Such information may be provided to the user by the display 54 and/or the signal device 44. In such exemplary combination mode embodiments, the information received from the imaging device 60, proximity sensor 61, and/or other like sensors of the temperature device 10 may be used by the controller 52 as described above with respect to, for example, FIGS. 3-7 and 9, as well as the exemplary noncontact modes of operation.

In still further exemplary embodiments, the temperature devices 10 of the present disclosure may include one or more ports, connectors, terminals, and/or other like connection devices configured to enable communication between the temperature device 10 and one or more separate devices. For example, in the noncontact-based embodiments described herein, the sensor 32 and corresponding optical components 36 may be omitted from the temperature device 10. Additionally, as discussed above with respect to at least the exemplary temperature device 10 shown in FIG. 8, the shaft 19, handle 20, and/or the entire probe 8 may be omitted. In such embodiments, the handpiece 50 may include one or more connection devices (not shown) enabling connection and/or communication between the handpiece 50 and a separate contact-based probe 8 or other like contact-based sensing device. In such embodiments, one or more components of the contact-based sensing devices may be disposable.

Additionally, in one or more of the exemplary contact-based embodiments described herein, a contact-based temperature device 10 may include one or more ports, connectors, terminals, and/or other like connection devices configured to enable communication between the contact-based temperature device 10 and one or more separate noncontact-based temperature sensing devices. Such noncontact-based temperature sensing devices may include, for example, one or more sensors 33 configured to determine a physical characteristic of the patient without contacting the patient.

In additional exemplary embodiments, the temperature devices 10 described herein may be capable of automatically configuring and/or reconfiguring themselves depending on the age, gender, and/or other physical characteristics of the patient. For example, such temperature devices 10 may be configured to make a noncontact-based determination of one or more physical characteristics of the patient. Such noncontact-based determinations may be made, for example, by the controller 52 in conjunction with the imaging device 60, sensor 33, and/or any other noncontact-based sensors of the temperature device 10. Such determinations may include, for example, capturing an image of the patient and, through one or more image recognition and/or image processing algorithms, determining an approximate age of the patient. Such images may include, for example, a visual image and/or a thermal image, and such algorithms may also be used to determine, for example, the gender of the patient. Once the gender and/or the approximate age of the patient has been determined, the temperature device 10 may automatically select an appropriate control configuration for future temperature determinations and/or other physical characteristic determinations. For example, if the temperature device 10 determines that the patient is an adult, the temperature device 10 may, in response to the determination, automatically utilize one or more core temperature determination algorithms and/or physical characteristic determination algorithms tailored toward treatment and/or diagnosis of adult patients. Alternatively, if the temperature device 10 determines that the patient is a pediatric patient, the temperature device 10 may, in response to the determination, automatically utilize one or more core temperature determination algorithms and/or physical characteristic determination algorithms tailored toward treatment and/or diagnosis of pediatric patients. A similar "tailored" algorithm and/or process may be employed by the temperature device 10 in response to the determination of patient gender.

Figure 11:
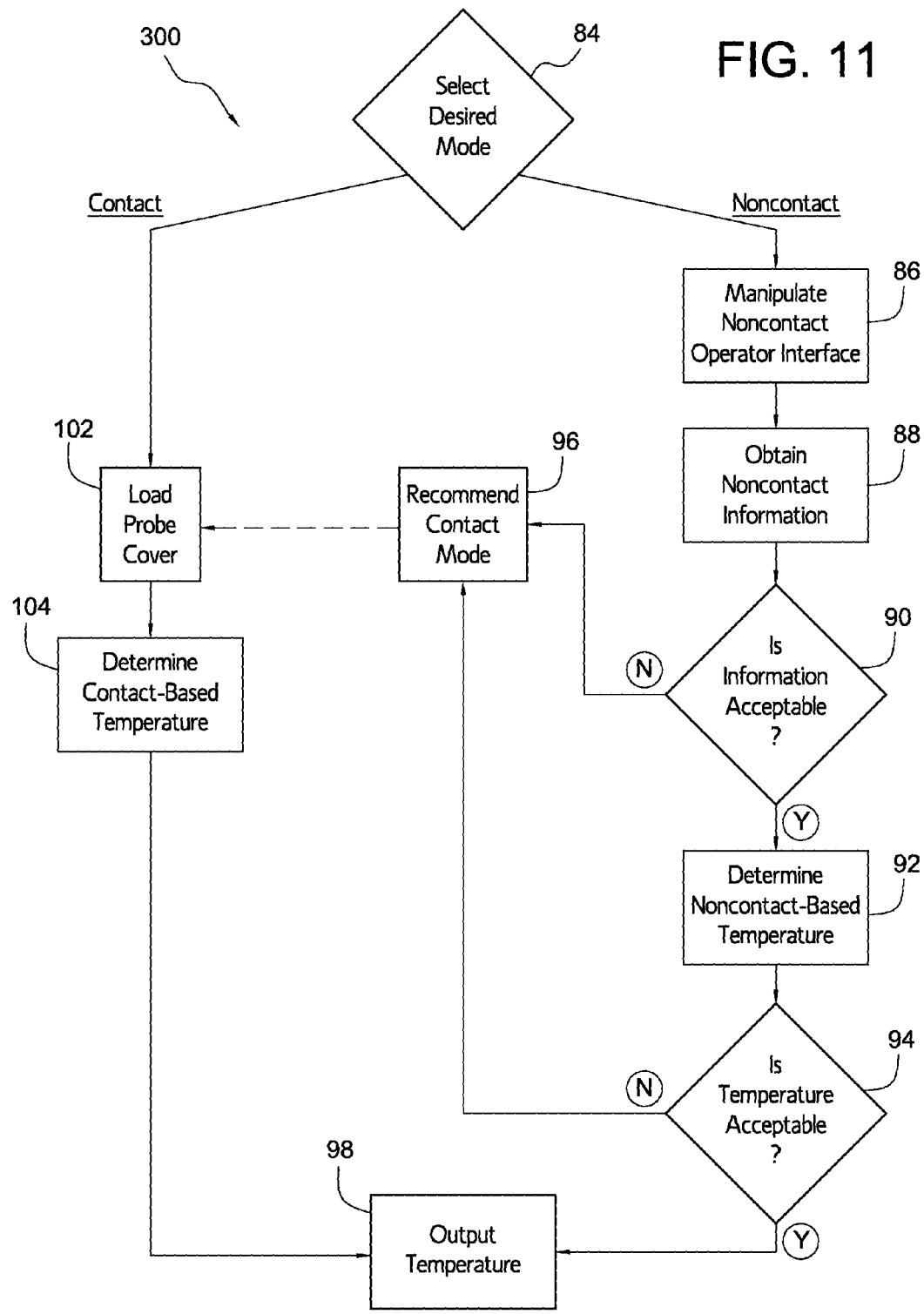
FIG. 11 illustrates a flowchart outlining an exemplary method of use associated with the present disclosure.

In still further exemplary embodiments of the present disclosure, the temperature devices 10 of the present disclosure may be configured to enable the user to select and switch between contact, noncontact, and/or combination-based modes of operation. The flowchart 300 shown in FIG. 11 illustrates an exemplary method of use associated with the temperature devices 10 described herein. Although the method shown in FIG. 11 illustrates contact and noncontact-based modes of operation, in further embodiments, such exemplary methods may also include enabling the user to select and/or switch to one of the combination-based modes of operation described above. As shown in FIG. 11, a user may begin an exemplary workflow by selecting a desired mode of operation (Step: 84). For example, at Step: 84, the user may select between the noncontact, contact, and/or combination-based (not shown) modes of operation described herein. The user may select such a desired mode by pressing, switching, and/or otherwise manipulating an operator interface 22 associated with mode selection.

If the user selects a noncontact mode of operation at Step: 84, control may proceed to Step: 86 wherein the user may manipulate one or more operator interfaces 22 of the temperature device 10 associated with determining noncontact information such as a physical characteristic of the patient. For example, the user may press one of the operator interfaces 22 associated with activating sensor 33, imaging device 60, proximity sensor 61, and/or other noncontact components of the temperature device 10. Upon activation at Step: 86, such components may obtain noncontact information associated with the patient at Step: 88. For example, such components may sense, measure, observe, read, and/or otherwise survey the outer surface 70 at Step: 88, and may send one or more corresponding signals to controller 52. At Step: 88, controller 52 may utilize noncontact information contained in such signals as inputs to one or more algorithms, look-up tables, maps, and/or other like means, and may determine one or more physical characteristics, or other noncontact information, associated with the patient using such means. For example, at Step: 88, the proximity sensor 61 may determine one or more alignment parameters associated with a position of the temperature device 10 relative to the patient. In such an exemplary embodiment, such an alignment parameter may include, among other things, the distance D between the temperature device 10 and the patient.

At Step: 90, the controller 52 may determine whether the information obtained at Step: 88 is within one or more acceptable ranges, above or below one or more predetermined thresholds, and/or is otherwise acceptable. For example, if an alignment parameter or other information determined at Step: 88 is outside of a predetermined acceptable range (Step: 90—No), control may proceed to Step: 96 wherein the controller 52 may recommend that the user switch from the noncontact mode to the contact mode of operation. Such recommendations may be made to the user via one or more of the display 54 and the signal device 44. If the user accepts such a recommendation the user may manipulate an operator interface 22 in order to switch from noncontact mode to contact mode, and control may proceed to Step: 102.

If, on the other hand, the alignment parameter or other information determined at Step: 88 is within a predetermined acceptable range (Step: 90—Yes), control may proceed to Step: 92 where the sensor 33 and/or controller 52 may determine a noncontact-based temperature of the patient. For example, the sensor 33 may be activated to collect radiation 62 emitted by the forehead, eyes, sinus area, and/or other locations on the outer surface 70 of the patient. Signals indicative of the patient measurement site temperature may be sent to the controller 52 by the sensor 33, and the controller 52 may assist in estimating a core temperature of the patient at Step: 92 based such signals.

At Step: 94, the controller 52 may determine whether the noncontact-based temperature determined at Step: 92 is within one or more acceptable ranges, above or below one or more predetermined thresholds, and/or is otherwise acceptable. If the determined temperature is outside of a predetermined acceptable range (Step: 94—No), control may proceed to Step: 96 wherein the controller 52 may recommend that the user switch from the noncontact mode to the contact mode of operation. If, on the other hand, the determined noncontact-based temperature is within a predetermined acceptable range (Step: 94—Yes), control may proceed to Step: 98 where the temperature determined at Step: 92 may be output to the user. At Step: 98, the determined noncontact-based temperature may be output to the user via one or more of the display 54 and the signal device 44.

If the user selects the contact mode of operation at Step: 84 or if the user accepts the recommendations made at Step: 96, control may proceed to Step: 102 where the user may load a probe cover 30 onto a portion of the temperature device 10. For example, with respect to the exemplary embodiment of FIG. 1, the user may position a probe cover 30 over the head 18, and may releasably couple the probe cover 30 to the temperature device 10 as described above. Alternatively, with respect to the exemplary embodiment of FIG. 8, the user may insert the shaft 19 of probe 8 into the probe cover 30, and may releasably couple the probe cover 30 to the temperature device 10 as described above.

At Step: 104, the probe cover 30 may be placed into contact with a patient measurement site to facilitate determining a contact-based temperature of the patient. For example, as described above with respect to FIG. 1, at least a portion of the probe cover 30 may be inserted into an ear canal of the patient such that the tip 58 is disposed proximate the tympanic membrane of the patient. The probe cover 30 and/or the sensor 32 may be positioned such that the probe cover 30 is in contact with the ear and/or ear canal, and the tympanic membrane is disposed at least partially within the field of view of the sensor 32. Alternatively, as described above with respect to FIG. 8, the probe cover 30 may be inserted into an axilla area, a rectal cavity, an oral cavity, and/or other like patient measurement site such that the tip 58 is disposed in contact with the measurement site. Once the probe cover 30 has been placed in contact with the patient measurement site, the sensor 32 may sense a temperature indicative of a temperature of the patient measurement site. Signals indicative of the patient measurement site temperature may be sent to the controller 52 by the sensor 32, and the controller 52 may assist in estimating the core temperature based on this sensed temperature. At Step: 98, the determined contact-based temperature may be output to the user via one or more of the display 54 and the signal device 44.

Other embodiments of the present disclosure will be apparent to those skilled in the art from consideration of the specification and practice of the embodiments described herein. It is intended that the specification and examples be considered as exemplary only, with a true scope and spirit of the present disclosure being indicated by the following claims.

What is claimed is:

1. A method of manufacturing a temperature measurement device, comprising:
providing a first sensing element configured to determine a temperature of a first anatomical structure of a patient without contacting the first anatomical structure;
providing a second sensing element configured to determine a temperature of a second anatomical structure of the patient without contacting the second anatomical structure, wherein the second anatomical structure is different from the first anatomical structure;
associating a controller with at least one of; the first sensing element and the second sensing element;
connecting an imaging device to the controller; and
programming the controller to:
capture, using the imaging device, a non-thermal image of the patient including the first and second anatomical structures,
identify, using the non-thermal image, a location of the first anatomical structure and a location of the second anatomical structure;
measure a temperature of the first anatomical structure by focusing a field of view of the first sensing element on the location of the first anatomical structure;
measure a temperature of the second anatomical structure by focusing a field of view of the second sensing element on the location of the second anatomical structure, and
determine a temperature of the patient based on the temperatures of at least one of the first and second anatomical structures.

2. The method of claim 1, further including connecting a display to the controller, the display being configured to display the non-thermal image of the patient.

3. The method of claim 1, wherein the at least one of the first and second anatomical structures comprises a sinus region of the patient.

4. The method of claim 1, wherein at least one of the first and second sensing elements comprises a sensing element in an array of sensing elements.

5. The method of claim 1, further including configuring the controller to render the non-thermal image on a display simultaneously with a visual illustration of an alignment parameter, the visual illustration indicating whether the device is located within a predetermined position range, relative to the patient, associated with a third sensor of the device.

6. The method of claim 1, further including configuring the controller to maintain the first sensing element inactive until the first anatomical structure is brought within the field of view of the first sensing element, and activating the first sensing element in response to the first anatomical structure being within the field of view of the first sensing element.

7. The method of claim 1, further including configuring the controller to determine one of an approximate age of the patient and a gender of the patient, and automatically selecting, with the controller, a control configuration of the device based on the one of the approximate age and the gender.

8. The method of claim 1, further including configuring the controller to output a signal indicating whether the device is disposed within a predetermined position range extending from the device to the patient, wherein the signal comprises at least one of a visual signal and an audible signal.

9. A temperature measurement device, comprising:
a first sensing element configured to determine a temperature of a first location on a measurement site of a patient without contacting the first location;
a second sensing element configured to determine a temperature of a second location on the measurement site of the patient different from the first location without contacting the second location;

an imaging device; and a controller in communication with the imaging device, the first sensing element, and the second sensing element, the controller being configured to:
  identify the first location using a digital photo of the patient captured by the imaging device;
  identify the second location using the digital photo;
  measure a temperature of the first location by focusing a field of view of the first sensing element on the first location;
  measure a temperature of the second location by focusing a field of view of the second sensing element on the second location; and
  determine a temperature of the patient based on the temperatures of at least one of the first and second locations.

10. The device of claim 9, wherein the imaging device is configured to direct signals to the controller; the device further including
  a display in communication with the controller, the display being configured to display a visual image of the measurement site based on the signals.

11. The device of claim 9, further comprising a sensor configured to determine an alignment parameter indicative of a position of the device relative to the patient, and a signal device configured to indicate whether the alignment parameter is within a predetermined parameter range at least partly in response to a determination of the alignment parameter made by the sensor.

12. The device of claim 9, wherein at least one of the first and second sensing elements comprises a sensing element in an array of sensing elements, and wherein the first and second locations comprise locations at a nose region on a face of the patient.

13. The device of claim 9, wherein the device comprises a handpiece including a display, the controller including an image processor configured to assist in forming a visual image of the patient on the display.

14. A method of determining a temperature of a patient, comprising:
  capturing a digital photo of the patient with an imaging device;
  identifying, with a temperature device, a first location on an outer surface of the patient using the digital photo;
  identifying, with the temperature device, a second location on the outer surface using the digital photo;
  measuring a first temperature of the patient with the temperature device, without contacting the patient with the device, by focusing a field of view of a first sensing element of the temperature device on the first location;
  measuring a second temperature of the patient with the temperature device, without contacting the patient with the device, by focusing a field of view of a second sensing element of the temperature device on the second location;
  determining an orientation of the device relative to the patient while measuring at least one of the first temperature and the second temperature; and
  determining a third temperature based on the orientation of the device, and at least one of the first temperature and the second temperature.

15. The method of claim 14, wherein the first and second locations comprise locations at an eye region of a face of the patient.

16. The method of claim 14, further including assigning a weight factor to at least one of the first temperature, the second temperature and the orientation of the device, and determining the temperature value based on the weight factor.

17. The method of claim 14, wherein the orientation of the device comprises at least one of a distance between the device and the patient, and an angle formed between the device and a plane substantially defined by the outer surface.

18. The method of claim 14, wherein the first sensing element comprises an element of a sensor array of the device.

19. The method of claim 14, wherein the first sensing element comprises an infrared sensing element, and the first location on the outer surface comprises a sinus region of the patient illustrated in the image, the image being generated using an imaging device of the temperature device.

20. The method of claim 14, wherein the third temperature comprises a core temperature of the patient.

21. A temperature measurement device, comprising:
  a first sensing element configured to determine a temperature of a first location on a measurement site of a patient without contacting the first location;
  a second sensing element configured to determine a temperature of a second location on the measurement site of the patient different from the first location without contacting the second location;
  an imaging device configured to capture a visual image of the measurement site; and
  a controller in communication with the first sensing element, the second sensing element, and the imaging device, the controller being configured to:
    identify the first location using the visual image;
    identify the second location using the visual image;
    measure a temperature of the first location by focusing a field of view of the first sensing element on the first location;
    measure a temperature of the second location by focusing a field of view of the second sensing element on the second location; and
    determine a temperature of the patient based on the temperatures of at least one of the first and second locations.

* * * * *